United States Patent [19]

Adelstein et al.

[11] Patent Number: 4,687,775

[45] Date of Patent: Aug. 18, 1987

[54] 2-[(IMIDAZO[1,2-A]PYRIDINYLMETHYL)-SULFINYL]-1H-BENZIMIDAZOLES

[75] Inventors: Gilbert W. Adelstein, Evanston; Alan E. Moormann, Skokie; Stella S. T. Yu, Morton Grove, all of Ill.

[73] Assignee: G. D. Searle & Co., Chicago, Ill.

[21] Appl. No.: 887,842

[22] Filed: Jul. 17, 1986

[51] Int. Cl.⁴ .................. A61K 31/435; C07D 471/04
[52] U.S. Cl. .................................. 514/300; 546/121
[58] Field of Search ..................... 546/121; 514/300

[56] References Cited

U.S. PATENT DOCUMENTS

| | | | |
|---|---|---|---|
| 4,045,563 | 8/1977 | Berntsson et al. | 424/263 |
| 4,045,564 | 8/1977 | Berntsson et al. | 424/263 |
| 4,182,766 | 1/1980 | Krassó et al. | 424/263 |
| 4,248,880 | 2/1981 | Krassó et al. | 424/263 |
| 4,255,431 | 3/1981 | Junggren et al. | 424/263 |
| 4,327,102 | 4/1982 | Crossley | 424/263 |
| 4,337,257 | 6/1982 | Junggren et al. | 424/263 |
| 4,359,465 | 11/1982 | Ruwart | 426/263 |
| 4,394,509 | 7/1983 | Crossley | 546/339 |
| 4,472,409 | 9/1984 | Senn-Bilfinger | 424/263 |

FOREIGN PATENT DOCUMENTS

| | | |
|---|---|---|
| 903128 | 12/1985 | Belgium . |
| 127763 | 12/1984 | European Pat. Off. . |
| 130729 | 1/1985 | European Pat. Off. . |
| 3415971 | 8/1984 | Fed. Rep. of Germany . |
| 416649 | 1/1981 | Sweden . |
| 2134523 | 8/1984 | United Kingdom . |
| 2137616 | 8/1984 | United Kingdom . |

OTHER PUBLICATIONS

J. G. Spenney, "Biochemical Mechanisms of Acid Secretion by Gastric Parietal Cells", *J. Clin. Gastro.* 5 (suppl. 1), 7–15 (1983).

B. Beilenson & F. M. Hamer, "Thiazenocyanines, Part I, Carbocyanines Containing the 2:4–Benzthiazine Nucleus", *J. Chem. Soc.*, 98–102 (1942).

J. Chandra Rajan & L. Klein, "Determination of Inorganic Phosphorus in the Presence of Organic Phosphorus"..., *Anal. Biochem.*, 92, 407–412 (1976).

*Primary Examiner*—Henry R. Jiles
*Assistant Examiner*—Bernard I. Dentz
*Attorney, Agent, or Firm*—Richard E. L. Henderson; Paul D. Matukaitis

[57] ABSTRACT

This invention relates to 2-[(imidazo[1,2-a]pyridinylmethyl)-sulfinyl]-1H-benzimidazoles that are useful in the treatment and prevention of ulcers.

18 Claims, No Drawings

2-[(IMIDAZO[1,2-A]PYRIDINYLMETHYL)SULFINYL]-1H-BENZIMIDAZOLES

BACKGROUND OF THE INVENTION (a) Field of the Invention

This invention relates to compounds that are useful in the treatment and prevention of ulcers. More particularly, this invention relates to 2-[(imidazo[1,2-a]pyridinylmethyl)sulfinyl]-1H-benzimidazoles that inhibit gastric acid secretion and which are, therefore, useful in the treatment of peptic ulcers. The compounds of this invention directly inhibit acid secretion by parietal cells of the stomach through inhibition of (H+ +K+)-ATPase. For review, see, e.g., J. G. Speeney, "Biochemical Mechanisms of Acid Secretion by Gastric Parietal Cells," *J. Clin. Gastro.* 5 (Suppl. 1), 7–15 (1983). In addition, some of the compounds of this invention also exert cytoprotective activity. For review of cytoprotection, see, e.g., U.S. Pat. No. 4,359,465.

(b) Prior Art

Heterocyclylalkylsulfinylbenzimidazoles have been disclosed as gastric acid secretion inhibitors. See U.S. Pat. Nos. 4,472,409, 4,394,509, 4,337,257, 4,327,102, 4,255,431, 4,045,564, and 4,045,563; British Patent No. 2,134,523; German Offenlegungschrift No. 3,415,971, and Swedish Patent No. 416649. Some heterocyclylalkylsulfinylbenzimidazoles have also been disclosed as cytoprotective agents. See U.S. Pat. No. 4,359,465. The following structure is illustrative of compounds disclosed in these patents:

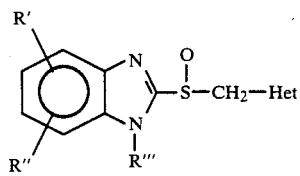

wherein R' and R" represent hydrogen, alkyl, halogen, trifluoromethyl, cyano, carboxy, hydroxy, acyl, and the like; R''' represents hydrogen, alkyl, acyl, alkoxysulfonyl, and the like; and Het represents heterocyclic groups containing at least one endocyclic (ring) nitrogen. No compound disclosed in these patents includes an imidazo[1,2-a]pyridine ring system, a feature characteristic of the compounds of the present invention.

Heterocyclylalkylsulfinylnaphth[2,3-d]imidazoles have also been disclosed as gastric acid secretion inhibitors. See U.S. Pat. Nos. 4,248,880 and 4,182,766. The compounds disclosed in these patents are related to those illustrated in the above structure, except for having a substituted naphth[2,3-d]imidazole group instead of the benzimidazole group. Similarly, other heterocyclylalkylsulfinylbenzimidazoles having a ring fused to the benzimidazole group have been disclosed as gastric acid secretion inhibitors and cytoprotective agents. See European Patent Application Nos. 130,729 and 127,763. Because of the additional ring fusions of these compounds, as well as for the same reasons stated in the preceding paragraph, the compounds of the present invention are structurally distinguished from prior art compounds cited.

Benzylsulfinylbenzimidazoles have also been disclosed as antiulcer agents. Belgian Patent 903,128. No compounds disclosed in the Belgian patent contain an imidazopyridine ring system, a feature characteristic of the compounds of this invention.

SUMMARY OF THE INVENTION

The invention relates to compounds of Formula I:

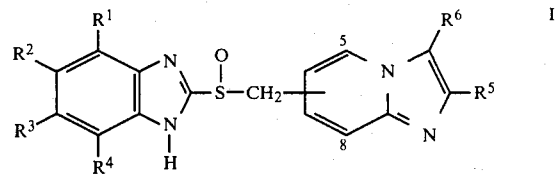

or the pharmaceutically acceptable acid addition salts thereof; or the pharmaceutically acceptable base addition salts thereof; wherein $R^1$, $R^2$, $R^3$, and $R^4$ are independently:
(a) hydrogen;
(b) $C_1$–$C_{10}$ alkyl;
(c) $C_1$–$C_6$ alkoxy;
(d) $C_1$–$C_4$ fluorinated alkyl; or
(e) halogen; and wherein $R^5$ and $R^6$ are independently:
(a) hydrogen;
(b) $C_1$–$C_{10}$ alkyl; or
(c) phenyl or phenyl substituted with 1 to 3 substituents selected from the group:
  (i) $C_1$–$C_{10}$ alkyl;
  (ii) $C_1$–$C_6$ alkoxy;
  (iii) $C_1$–$C_4$ fluorinated alkyl;
  (iv) halogen;
  (v) nitro, with the proviso that only one such substituent may be nitro; or
  (vi) $C_2$–$C_6$ alkoxycarbonyl.

Although the structure shown for Formula I indicates one tautomeric form, it is understood that this representation is for convenience only and that the scope of this invention includes as equivalents all tautomeric forms of the compounds of this invention.

The term "$C_1$–$C_{10}$ alkyl" refers to straight or branched chain alkyl groups having from 1 to 10 carbon atoms, also referred to as lower alkyl. Examples of $C_1$–$C_{10}$ alkyl are methyl, ethyl, propyl, butyl, pentyl, hexyl, heptyl, octyl, nonyl, decyl, and the isomeric forms thereof.

The term "$C_1$–$C_6$ alkoxy" refers to straight or branched chain alkoxy groups having from 1 to 6 carbon atoms. Examples of $C_1$–$C_6$ alkoxy are methoxy, ethoxy, propoxy, butoxy, pentoxy, hexoxy, and the isomeric forms thereof.

The term "$C_1$–$C_4$ fluorinated alkyl" refers to straight or branched chain alkyl groups in which one or more hydrogen atoms are replaced with fluorine atoms. Examples of $C_1$–$C_4$ fluorinated alkyl are fluoromethyl, difluoromethyl, trifluoromethyl, 1- or 2-fluoroethyl, 1,1-difluoroethyl, 2,2,2-trifluoroethyl, perfluoroethyl; other similarly monofluorinated, polyfluorinated, and perfluorinated ethyl, propyl, and butyl groups; and the isomeric forms thereof.

The term "$C_2$–$C_6$ alkoxycarbonyl" refers to straight of branched chain alkoxycarbonyl groups having from 2 to 6 carbon atoms. Examples of $C_2$–$C_6$ alkoxycarbonyl are methoxycarbonyl, ethoxycarbonyl, propoxycarbonyl, butoxycarbonyl, pentoxycarbonyl, and the isomeric forms thereof.

Examples of halogen are fluorine, chlorine, bromine, and iodine.

The term "pharmaceutically acceptable acid addition salt" refers to a salt prepared by contacting a compound of Formula I with an acid whose anion is generally considered suitable for human consumption. Examples of pharmacologically acceptable acid addition salts include the hydrochloride, hydrobromide, hydroiodide, sulfate, phosphate, acetate, propionate, lactate, maleate, malate, succinate, and tartrate salts.

The term "pharmaceutically acceptable base addition salt" refers to a salt prepared by contacting a compound of Formula I with a base whose cation is generally considered suitable for human consumption. Examples of pharmacologically acceptable base addition salts include lithium, sodium, potassium, magnesium, calcium, titanium, ammonium, alkylammonium, dialkylammonium, trialkylammonium, tetraalkylammonium, and guanidinium salts.

DESCRIPTION OF THE INVENTION

The compounds of this invention may be prepared by the methods illustrated in the following Schemes. Unless otherwise specified, the various substituents are defined as for Formula I, above. Schemes A and B illustrate two preferred general methods for preparing the sulfoxide compounds of this invention, Formula I, by way of thio intermediates of Formula VI. One preferred general method, illustrated by Scheme A, involves forming the imidazo[1,2-a]pyridine moiety in a cyclization reaction performed after an initial S-alkylation step.

SCHEME A

Thio intermediates of Formula VI may be prepared by at least two routes based on Scheme A, each of which involves S-alkylation of a 2-mercaptobenzimidazole of Formula II with a compound of Formula III to form an intermediate of Formula IV. In one route, the 2-mercaptobenzimidazole of Formula II reacts with a halomethyl-2-pyridinamine (Formula III in which Y is a halogen, preferably chlorine or bromine, and Z is hydrogen or an acyl group) in a suitable organic solvent at room temperature. The halomethyl-2-pyridinamine of Formula III is preferably used as an N-acylated derivative, wherein Z is an acyl group, preferably $C_2$–$C_6$ alkanoyl. The term "$C_2$–$C_6$ alkanoyl" refers to straight or branched chain alkanoyl groups having from 2 to 6 carbon atoms. Examples of $C_2$–$C_6$ alkanoyl are acetyl, propanoyl, butanoyl, pentanoyl, hexanoyl, and the isomeric forms thereof. Preferred alkanoyl groups are trimethylacetyl or propanoyl. Suitable organic solvents for the reaction are organic liquids in which reactants may be dissolved or suspended but which are otherwise chemically inert. Examples of suitable organic solvents include N,N-dialkylformamides; lower alkanols, such as methanol, ethanol, propanol, isopropyl, alcohol, and the like; and other solvents known in the art.

SCHEME A

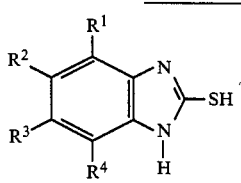

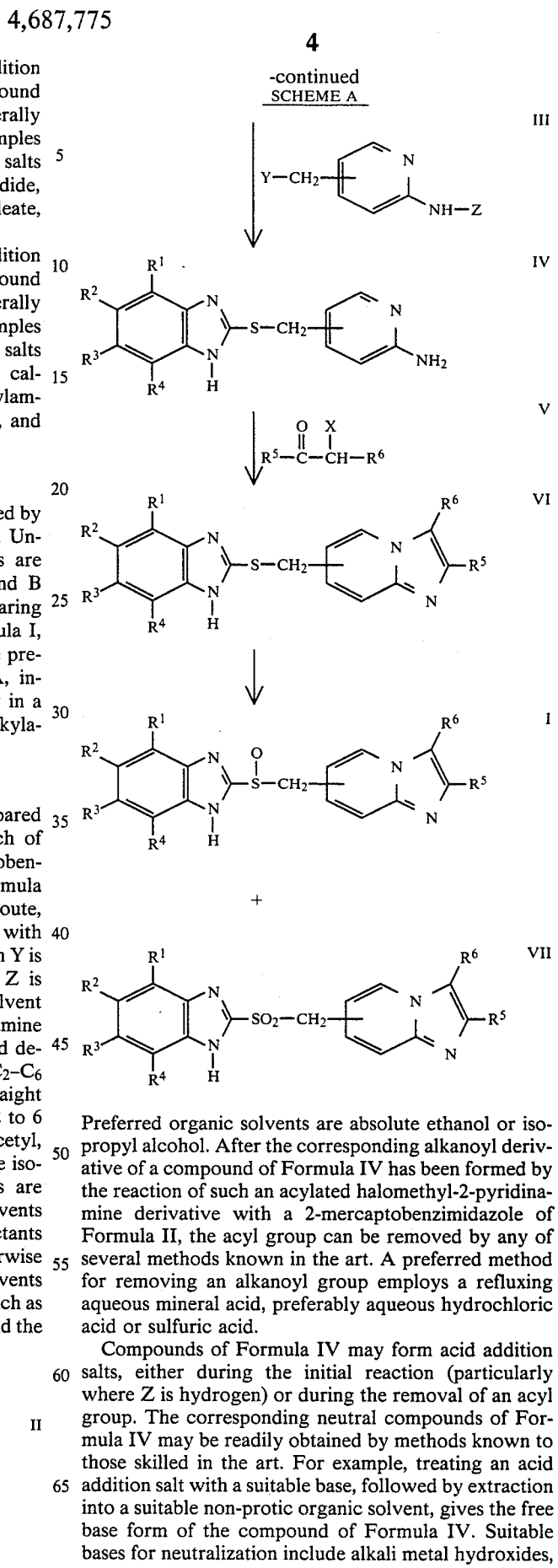

Preferred organic solvents are absolute ethanol or isopropyl alcohol. After the corresponding alkanoyl derivative of a compound of Formula IV has been formed by the reaction of such an acylated halomethyl-2-pyridinamine derivative with a 2-mercaptobenzimidazole of Formula II, the acyl group can be removed by any of several methods known in the art. A preferred method for removing an alkanoyl group employs a refluxing aqueous mineral acid, preferably aqueous hydrochloric acid or sulfuric acid.

Compounds of Formula IV may form acid addition salts, either during the initial reaction (particularly where Z is hydrogen) or during the removal of an acyl group. The corresponding neutral compounds of Formula IV may be readily obtained by methods known to those skilled in the art. For example, treating an acid addition salt with a suitable base, followed by extraction into a suitable non-protic organic solvent, gives the free base form of the compound of Formula IV. Suitable bases for neutralization include alkali metal hydroxides, such as lithium, sodium, or potassium hydroxide; alkali metal carbonates or bicarbonates, such as lithium, sodium, or potassium carbonate, or lithium, sodium, or potassium bicarbonate; and tertiary amines, such as triethylamine, tributylamine, N-methylmorpholine, and the like; and other such bases known in the art. Preferred bases include sodium carbonate or potassium carbonate. Suitable non-protic organic solvents for extraction include alkanes and cycloalkanes; ethers and cyclic ethers; alkyl alkanoate esters, such as ethyl acetate and the like; aromatic hydrocarbons; halocarbons, such as chloroform, dichloromethane, ethylene dichloride, and the like; and other solvents known in the art. Preferred non-protic organic solvents include ethyl acetate, dichloromethane, and chloroform. Compounds that crystallize spontaneously upon addition of the organic solvent may be collected without completing the extraction procedure. If desired, compounds of Formula IV may be purified by methods known in the art, including recrystallization and chromatography.

A second and generally preferred route based on Scheme A and using intermediates of Formula IV involves acid-catalyzed S-alkylation of a 2-mercaptobenzimidazole of Formula II with an hydroxymethyl-2-pyridinamine (Formula III in which Y is OH and Z is hydrogen) or an alkanoyloxymethyl-2-pyridinamine (Formula III in which Y is alkanoyloxy, preferably acetoxy, and Z is hydrogen). Preferred conditions include heating a mixture of compounds of Formulas II and III in a suitable acidic medium. A suitable acidic medium is a chemical substance or mixture of chemical substances that dissolves the compounds of Formulas II and III and is sufficiently acidic to induce the desired reaction, but which does not itself form significant quantities of byproducts by reaction with the compounds of Formulas II and III. Preferred acidic media include mixtures of hydrogen halides (such as hydrogen chloride or hydrogen bromide) in glacial acetic acid or aqueous hydrohalic acids (such as hydrochloric or hydrobromic acid) in acetic acid. After the reaction is quenched by pouring the mixture over ice and the mixture is neutralized with a suitable base (such as potassium carbonate), intermediates of Formula IV may be isolated and purified by methods known in the art, including recrystallization and chromatography.

Cyclization of the aminopyridine moiety of intermediates of formula IV gives thio intermediates of Formula VI. A preferred cyclization method involves reaction of intermediates IV with haloketones or haloaldehydes of Formula V (wherein X is a halogen, preferably chloine or bromine) and may be performed either in a suitable solvent or without such a solvent. Suitable solvents for cyclization are liquids in which reactants may be dissolved or suspended but which are otherwise chemically inert. Examples of suitable solvents include water; organic liquids, preferably alcohols; mixtures of water and water-miscible organic liquids; and other such solvents known in the art. Preferred solvents include water, alcohols (preferably methanol or ethanol), and aqueous alcohol mixtures. Where such a solvent is used, cyclization may be performed either with a suitable base added or without such a base. Suitable bases for cyclization are chemical compounds that are sufficiently basic to promote the cyclization but which do not themselves form significant quantities of byproducts by reaction with reactants or desired products. Examples of suitable bases include alkali metal carbonates or bicarbonates, such as lithium, sodium, or potassium carbonate, or lithium, sodium, or potassium bicarbonate; and tertiary amines, such as triethylamine, tributylamine, N-methylmorpholine, and the like. Preferred bases include alkali metal bicarbonates, preferably sodium bicarbonate. Thio intermediates of Formula VI are isolated as precipitates from the reaction mixture or, where precipitation does not occur, by evaporation of the reaction solvent. Purification may be effected using methods known in the art, including recrystallization and chromatography.

Cyclization of intermediates of Formula IV may also be performed without solvent being added, particularly where the haloketone or haloaldehyde of Formula V is a liquid. To shorten reaction times, the reaction mixture may optionally be heated, preferably in the range of about 50° to 100° C. The reaction may also be facilitated by addition of an iodide salt, preferably sodium or potassium iodide. Isolation and purification of thio interediates of Formula VI may be effected using methods known in the art, including solvent-solvent extraction, recrystallization, and chromatography.

The sulfoxide compounds of this invention, Formula I, may be prepared by oxidation of the thio intermediates of Formula VI using methods known to those skilled in the art. Commonly used oxidizing agents include, for example, peracids, such as m-chloroperoxybenzoic acid; peresters; peroxides, such as hydrogen peroxide; sodium metaperiodate; selenium dioxide manganese dioxide: iodosobenzene: and the like. Preferred conditions for preparing sulfoxides of Formula I include oxidizing intermediates VI with an approxmately equimolar quantity of m-chloroperoxybenzoic acid in a suitable organic solvent at temperatures below 0°. Suitable organic solvents for the oxidation include alkanes and cycloalkanes; aromatic hydrocarbons; halocarbons, such as chloroform, dichloromethane, ethylene dichloride, and the like; and other solvents known in the art. A preferred organic solvent is dichloromethane. Oxidation is quenched by adding dimethylsulfide. The sulfoxides of Formula I may then be isolated and purified by methods known in the art, including recrystallization and chromatography.

Further oxidation of the sulfoxide compounds of Formula I yields corresponding sulfones of Formula VII. The sulfones may form in situ during the initial oxidation reaction of thio intermediates of Formula VI or may be prepared by a separate oxidation of isolated sulfoxides of Formula I. The sulfones of Formula VII may then be isolated and purified by methods known in the art, including recrystallization and chromatography. Where the sulfones of Formula VII are prepared along with sulfoxides of Formula I during the initial oxidation reaction, the preferred method of isolation is chromatography.

A second preferred general method for preparing the sulfoxide compounds of this invention, illustrated by Scheme B, involves forming an imidazo[1,2-a]pyridine precursor for use in a subsequent S-alkylation step.

SCHEME B

The imidazo[1,2-a]pyridine precursor of Formula IX (that is, Formula III wherein Z is hydrogen and, preferably, wherein Y is OH or alkanoyloxy) is prepared by the reaction of a compound of Formula VIII (preferably in which Y is OH or alkanoyloxy) and a haloketone or haloaldehyde of Formula V using the same method described above (see Scheme A) for preparing a compound of Formula VI from a compound of Formula IV.

Thio intermediates of Formula VI are then prepared by a reaction of the imidazo[1,2-a]pyridine precursor of Formula IX and a 2-mercaptobenzimidazole of Formula II using S-alkylation methods described above (see Scheme A) for preparing a compound of Formula IV. Sulfoxides of this invention, Formula I, and sulfones of Formula VII may then be prepared by the same methods described above.

SCHEME C

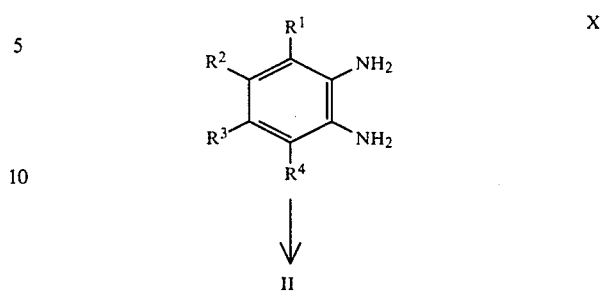

Halomethyl-2-pyridinamines of Formula III (wherein Y is a halogen, preferably chlorine or bromine) may be prepared by any of various methods known in the art. Scheme D, for example, illustrates a preferred preparation of $N^2$-alkanoyl halomethyl-2-pyridinamines of Formula XII (that is, Formula III in which Z is $C_2$–$C_6$ alkanoyl).

SCHEME D

Halogenation of $N^2$-alkanoyl methyl-2-pyridinamines of Formula XI using methods known in the art gives the corresponding $N^2$-alkanoyl halomethyl-2-pyridinamines of Formula XII (that is, Formula III in which Y is a halogen, preferably chlorine or bromine, and Z is $C_2$–$C_6$ alkanoyl, preferably acetyl). Preferred halogenation conditions employ a light-induced reaction with an N-halosuccinimide, preferably N-bromosuccinimide, in carbon tetrachloride containing a catalytic amount of 2,2′-azabisisobutyronitrile.

Halomethyl-2-pyridinamines of Formula III may also be prepared from corresponding hydroxymethyl-2-pyridinamines of Formula III (wherein Y is hydroxy) by synthetic methods well known in the art. For example, reaction of a hydroxymethyl compound with a suitable halogenating reagent in a suitable organic solvent will give the corresponding halomethyl-2-pyridinamine as a hydrohalide salt, typically a hydrochloride salt.

SCHEME B

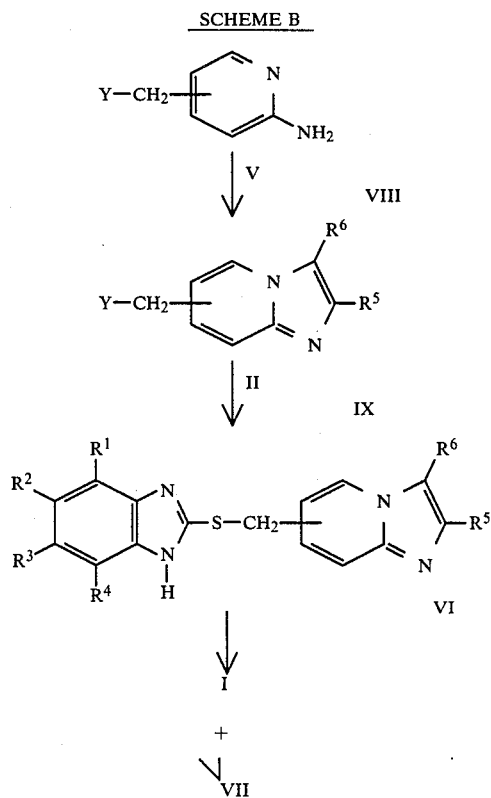

Acid addition salts of this invention may be prepared during the course of the reactions (as described above), by ion exchange from those salts using methods known in the art, or by acidification of free bases of the compounds. Base addition salts of this invention by methods known in the art, including those methods disclosed in British Pat. No. 2,137,616.

Although some 2-mercaptobenzimidazoles of Formula II (used as described above; see Schemes A and B) are commercially available, they may also be prepared by methods known to those skilled in the art. For example, Scheme C illustrates the preparation of 2-mercaptobenzimidazoles from substituted diaminobenzenes of Formula X.

SCHEME C

A preferred cyclization method employs an alkali metal alkylxanthate salt of the formula alkyl—O(C=O)S—$M^+$, where $M^+$ represents an alkali metal ion. Such alkylxanthate salts may be preformed by methods known in the art or may be formed in situ by mixing an alkali metal hydroxide (preferably sodium hydroxide) and carbon disulfide in an alcohol (preferably ethanol). Preferred alcoholic mixture of a diaminobenzene of Formula X with sodium or potassium ethylxanthate at reflux under an inert atmosphere, such as argon.

SCHEME D

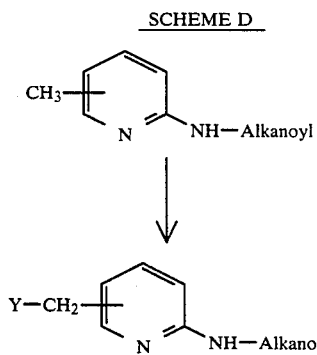

Suitable halogenating agents include thionyl chloride, phosphorus oxychloride, oxalyl chloride, and the like. Suitable organic solvents for halogenation include alkanes and cycloalkanes; ethers and cyclic ethers; aromatic hydrocarbons; halocarbons, such as chloroform, dichloromethane, ethylene dichloride, and the like; and other solvents known in the art. Preferred organic solvents include dichloromethane and chloroform. A related, and generally preferred, method involves heating an hydroxymethyl-2-pyridinamine in concentrated hydrochloric or hydrobromic acid at temperatures of 80° to 100°. See B. Beilenson and F. M. Hamer, *J. Chem. Soc.*, 98–102 (1942).

Hydroxymethyl-2-pyridinamines of Formula III (wherein Y is a hydroxy) and alkanoyloxymethyl-2-pyridinamines of Formula III (wherein Y is a alkanoyloxy) may be prepared by any of various methods known in the art. Scheme E, for example, illustrates two preferred preparations of hydroxymethyl-2-pyridinamines. The methods illustrated in Scheme E are best performed on compounds in which Z is $C_2$–$C_6$ alkanoyl.

SCHEME E

Hydroxylation of methyl-2-pyridinamines of Formula XIII using a trialkyl borate or trialkylborane and hydrogen peroxide gives the corresponding hydroxymethyl-2-pyridinamines of Formula XV.

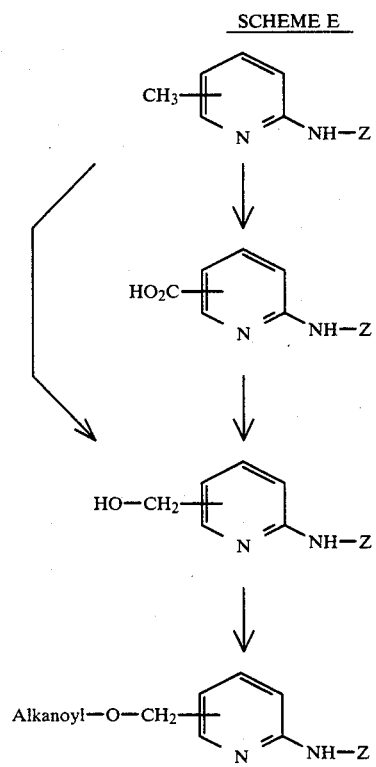

Preferred conditions involve an initial deprotonation at the methyl group using a suitable strong base in a suitable organic solvent maintained at temperatures below 0° C. Suitable strong bases are chemical compounds that are sufficiently basic to abstract a proton from the methyl group of a compound of Formula XIII so that the subsequent reaction with the trialkyl borate or trialkylborane can take place. Examples of suitable strong bases include alkali metal hydrides, such as sodium hydride and potassium hydride; alkali metal alkyls, such as n-butyllithium and t-butyllithium; and the like. Suitable organic solvents for deprotonation include alkanes and cycloalkanes; ethers and cyclic ethers; aromatic hydrocarbons; and other solvents known in the art. A preferred organic solvent is tetrahydrofuran. After deprotonation is effected, a trialkyl borate, preferably trimethyl borate, is added. Subsequent reaction with aqueous hydrogen peroxide gives the hydroxymethyl-2-pyridinamine of Formula XV.

Another preferred hydroxylation method involves an initial oxidation of methyl-2-pyridinamines of Formula XIII to carboxylic acids of Formula XIV using methods known in the art. A preferred oxidation employs potassium permanganate in water heated to about 50° to 80° C. The carboxylic acid may then be reduced to the corresponding hydroxymethyl-2-pyridinamine of Formula XV using reduction methods known in the art. Examples of reduction methods include reaction with lithium aluminum hydride, a borane, and the like. A preferred reduction method employs borane in tetrahydrofuran.

Alkanoyloxy compounds of Formula XVI in which Y is $C_2$–$C_6$ alkanoyloxy, preferably acetoxy, can be prepared by acylating corresponding hydroxymethyl compounds of Formula XV using methods well known in the art. For compounds of Formula XVI in which Z is hydrogen rather than alkanoyl, corresponding precursor compounds of Formula XV should first be protected with any of several acid sensitive N-protecting groups known in the art. The protecting group is then removed after the acylation step. Alternatively, such compounds of Formula XV in which Z is hydrogen may be O-acylated in an acidic medium to minimize N-acylation.

The preferred embodiments of this invention include compounds of the following general structure:

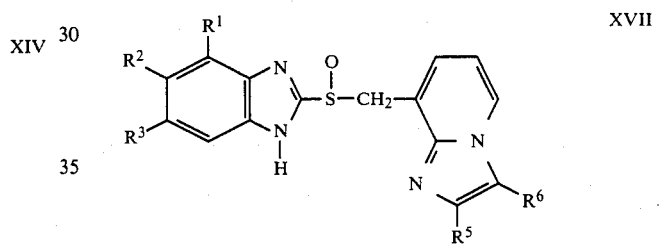

or the pharmaceutically acceptable acid addition salts thereof; wherein $R^1$, $R^2$, and $R^3$, are independently hydrogen, $C_1$–$C_{10}$ alkyl, $C_1$–$C_6$ alkoxy, trifluoromethyl, or chlorine; and wherein $R^5$ and $R^6$ are independently hydrogen, $C_1$–$C_{10}$ alkyl, phenyl, or phenyl substituted with any one of $C_1$–$C_{10}$ alkyl $C_1$–$C_6$ alkoxy, trifluoromethyl, chlorine, nitro, or $C_2$–$C_6$ alkoxycarbonyl.

The most preferred embodiments of this invention include compounds of the following general structure:

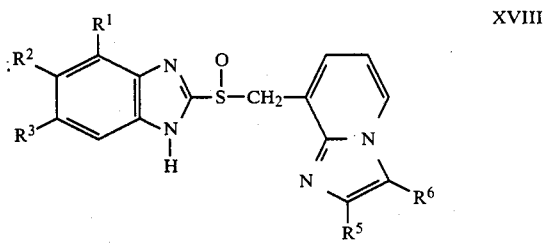

or the pharmaceutically acceptable acid addition salts thereof; wherein $R^1$ and $R^3$ are independently hydrogen or methyl; wherein $R^2$ is hydrogen, methyl, methoxy, ethoxy, trifluoromethyl, or chlorine; wherein $R^5$ is hydrogen or methyl; and wherein $R^6$ is hydrogen, methyl, phenyl, or phenyl substituted with any one of methyl, trifluoromethyl, chlorine, or methoxycarbonyl.

The compounds of this invention exhibited gastric antisecretory activity in canines, as indicated by inhibition in vitro of $(H^+ + K^+)$-ATPase obtained from canine gastric mucosa and by inhibition in vivo of gastric acid secretion in dogs. The antisecretory activity of the compounds of this invention illustrated in the Examples was tested by the following methods.

Inhibition of $(H^+ + K^+)$-ATPase from Canine Gastric Mucosa

Mongrel dogs weighing 15 to 25 kilograms were fasted for twenty-four hours, with water provided ad libitum. The animals were anesthetized with pentobarbital and the stomachs were removed. Subsequent tissue manipulations and subcellular fractionations were performed at 0° to 4° C. After the stomachs were cut open and rinsed with tap water, the antral and cardiac regions were removed and the remaining tissue was rinsed three times in saline. The glandular mucosa was removed mechanically, chopped finely in a medium containing 10 mM Tris hydrochloride (pH 7.4) and 250 mM sucrose, and homogenized. The homogenate was centrifuged at 20,000×g for twenty minutes and the pellet discarded. The supernatant was then centrifuged at 150,000×g for ninety minutes and the supernatant discarded. The pellet was resuspended in the Tris-HCl/sucrose medium by homogenization. Part (2 ml) of the resultant microsomal suspension was layered onto a step gradient consisting of 9 ml of 15% sucrose above 12 ml of 30% sucrose, each sucrose solution being buffered with 10 mM Tris hydrochloride (pH 7.4) containing 0.01% sodium azide. The microsomes retained at the 15%–30% sucrose interface, after centrifugation at 250,000×g for sixty minutes, were used as the source of $(H^+ + K^+)$-ATPase. Microsomal preparations were lyophilized, a process that assured potassium ion permiability, and stored at −10° until used.

$(H^+ K^+)$-ATPase activity for each test compound was determined, in duplicate, by measuring the release of inorganic phosphate, which was assayed according to the method of J. ChandraRajan and L. Klein. *Anal. Biochem.*, 72, 407–412 (1976). The $(H^+ + K^+)$-ATPase assay medium consisted of 20 mM Mes-Tris (pH 6.0), 5 mM magnesium chloride, 25 mM sucrose, and 4 mM Tris-ATP with or without 20 mM potassium chloride in a total volume of 2 ml. Microsomal suspensions (20 to 60 mcl, containing about 25 mcg protein) were added to the assay medium, without Tris-ATP, and then preincubated with a test compound for thirty minutes at 37°. The assay was initiated by adding Tris-ATP and the mixture was incubated another thirty minutes at 37°. A 200-mcl aliquot of the assay mixture was then added to 1.4 ml of a solution consisting of 0.1M sodium acetate (pH 4.0) and 10% sodium dodecylsulfate, followed by the addition of 200 mcl each of 1% ammonium molybdate and 1% ascorbic acid. At least fifteen minutes later, the optical absorbance at 870 nm (which was proportional to inorganic phosphate concentration up to 100 nmoles per tube, as determined by a standard curve) was obtained. Enzyme activity was linear with incubation time.

$(H^+ + K^+)$-ATPase activity is represented by the difference between the measured activities in the presence of potassium ion ($K^+$-stimulated) and in the absence of potassium ion (basal). The concentration of a test compound required to inhibit 50% of the $(H^+ + K^+)$-ATPase activity (i.e., the $IC_{50}$) was determined at least in duplicate using linear regression analysis of results obtained for three different compound concentrations ranging from 0.1 mcM to 0.2 mM. If the $IC_{50}$ for a test compound could not be determined for the concentration range tested, percent inhibition of $(H^+ + K^+)$-ATPase was obtained for the compound at 0.1 mM.

Inhibition of Gastric Acid Secretion in Gastric Fistula Beagle Dogs

Adult female beagle dogs weighing 6 to 11 kilograms obtained from Laboratory Research Enterprises (Kalamazoo, Mich.) or from Hazelton Research Animals (Cumberland, Va.) were surgically implanted with a simple Thomas-type gastric cannula. After recovery from surgery, the dogs were trained to stand quietly, fully conscious, in Pavlov-type dog restraining slings and were acclimated to intravenous infusion of histamine dihydrochloride. During the course of these studies, no dog was used more than once a week. All dogs were deprived of food, but not water, for 18 hours prior to each assay. Each dog was initially infused with 0.15M sodium chloride solution at a constant rate of 6.5 mg/hr. The volume of gastric secretions, collected in plastic bottles affixed to the cannula, were measured to the nearest 0.1 ml at 30 minute intervals. One of the following protocols was followed, depending on the route chosen for administration of test compound.

Intravenous dosing: Following a 30-minute basal secretion period, test compounds were administered intravenously (i.v.). At the end of an additional 30 minute period, the saline infusion was replaced with histamine dihydrochloride in saline administered at a rate 15 mcg per kilogram of body weight per hour. Histamine stimulation was maintained for a maximum of four hours during which time gastric secretions were collected every 30 minutes. The pH and titratable acidity were determined for samples from each collection period.

Intragastric dosing: Following a 30-minute basal secretion period, the collection bottles were removed, dosing plugs were inserted and test compounds were administered intragastrically (i.g.). At the end of a 30-minute drug absorption period, the stomachs were emptied, the collection bottles were reattached, and collections were resumed at 30-minute intervals. Simultaneously, the saline infusion was replaced with a continuous intravenous infusion of histamine dihydrochloride in saline administered for four hours at a rate 15 mcg per kilogram of body weight per hour.

Intraduodenal dosing: Dogs were also equipped with duodenal cannulas for intraduodenal (i.d.) administration of test compounds. Dosing was otherwise performed as described for intragastric dosing.

Data from each protocol were analyzed for three gastric sample variables: volume of gastric juice, acid concentration, and total acid output. Percent inhibition for each four-hour experimental period was determined for each parameter by comparison with 3 to 4 controls in which only food was given. Estimates of $ED_{50}$'s were determined from dose response curves.

By virtue of their gastric antisecretory activity, the compounds of Formula I are useful in treating ulcers in mammals. A physician or veterinarian of ordinary skill can readily determine whether a subject has ulcers. Regardless of the route of administration selected, the compounds of the present invention are formulated into pharmaceutically acceptable dosage forms by conventional methods known to those skilled in the art. The compounds may be formulated using pharmacologically acceptable acid addition or base addition salts.

Moreover, the compounds or their salts may be used in a suitable hydrated form.

The compounds can be administered in such oral dosage forms as tablets, capsules, pills, powders, granules, elixirs, or syrups, The compounds may also be administered intravascularly, intraperitoneally, subcutaneously, or intramuscularly, using forms known to the pharmaceutical art. In general, the preferred form of administration is oral. For the orally administered pharmaceutical compositions and methods of the present invention, the foregoing active ingredients will typically be administered in admixture with suitable pharmaceutical diluents, excipients, or carriers (collectively referred to herein as "carrier" materials) suitably selected with respect to the intended form of administration, that is, oral tablets, capsules, elixirs, syrups, and the like, and consistent with conventional pharmaceutical practices. For example, for oral administration in the form of tablets or capsules, the active drug components may be combined with any oral non-toxic pharmaceutically acceptable inert carrier such as lactose, starch, sucrose, cellulose, magnesium stearate, dicalcium phosphate, calcium sulfate, mannitol, and the like, or various combinations thereof; for oral administration in liquid form, the active drug components may be combined with any oral non-toxic pharmaceutically acceptable inert carrier such as water, saline, ethanol, polyethylene glycol, propylene glycol, corn oil, cottonseed oil, peanut oil, sesame oil, benzyl alcohol, various buffers, and the like, or various combinations thereof. Moreover, when desired or necessary, suitable binders, lubricants, disintegrating agents, and coloring agents can also be incorporated in the mixture. Suitable binders include starch, gelatin, natural sugars, corn sweeteners, natural and synthetic gums such as acacia, sodium alginate, carboxymethylcellulose, polyethylene glycol, and waxes, or combinations thereof. Lubricants for use in these dosage forms include boric acid, sodium benzoate, sodium acetate, sodium chloride, and the like, or combinations thereof. Disintegrators include, without limitation, starch, methylcellulose, agar, bentonite, guar gum, and the like, or combinations thereof. Sweetening and flavoring agents and preservatives can also be included where appropriate.

For intravascular, intraperitoneal, subcutaneous, or intramuscular administration, active drug components may be combined with a suitable carrier such as water, saline, aqueous dextrose, and the like.

By whatever route of administration selected, an effective but non-toxic quantity of the compound is employed in treatment. The dosage regimen for preventing or treating ulcers with the compounds of this invention is selected in accordance with a variety of factors, including the type, age, weight, sex, and medical condition of the patient; the severity of the condition; the route of administration; and the particular compound employed. An ordinarily skilled physician or veterinarian can readily determine and prescribe the effective amount of the drug required to prevent or arrest the progress of the condition. In so proceeding, the physician or veterinarian could employ relatively low doses at first and subsequently increase the dose until a maximum response is obtained. Dosages of the compounds of the invention may be in the range of about 1.0 mcg/kg to 500 mg/kg, preferably in the range of about 10 to 100 mg/kg orally or about 1.0 to 20 mg/kg intravenously.

The following examples further illustrate details for the preparation of the compounds of this invention. The invention, which is set forth in the foregoing disclosure, is not to be construed or limited either in spirit or in scope by these examples. Those skilled in the art will readily understand that known variations of the conditions and processes of the following preparative procedures can be used to prepare these compounds. All temperatures are degrees Celsius unless otherwise noted. Chromatographic isolation and purification of the compounds of this invention, where required, was effected using silica gel or basic alumina, with mixtures of ethyl acetate and hexane or ethanol and dichloromethane used as eluent (unless otherwise specified). The appropriate chromatographic system was chosen for each compound by comparing separations on thin-layer chromatography plates coated with silica gel or basic alumina.

DESCRIPTION OF THE PREFERRED EMBODIMENTS

EXAMPLE 1

2-[(imidazo[1,2-a]pyridin-8-ylmethyl)thio]-1H-benzimidazole 1/4 hydrate

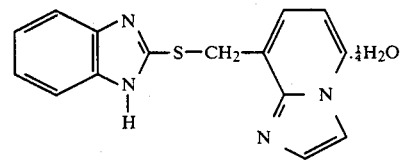

A mixture of 9.6 g (63 mmole) of 2-mercaptobenzimidazole and 7.7 g (62 mmole) of 3-hydroxymethyl-2-pyridinamine was dissolved in 60 ml of 48% aqueous hydrobromic acid and 60 ml of acetic acid and heated to reflux. After being cooled to room temperature, the mixture was poured into water and make alkaline with potassium carbonate. The oil that separated solidified upon addition of diethyl ether to the aqueous mixture. The solid was collected by filtration, washed with portions of diethyl ether and water, and air dried to yield 12.4 g of analytically pure 3-[(1H-benzimidazol-2-ylthio)methyl]-2-pyridinamine hemihydrate, as confirmed by the nmr and infrared spectra and by elemental analysis. [Calcd. for $C_{13}H_{12}N_4S.\frac{1}{2}H_2O$: C, 58.84; H, 4.93; N, 21.11; S, 12.08. Found: C, 59.06; H, 4.48; N, 20.82; S, 12.16.] A mixture of 4.0 g (15 mmole) of 3-[(1H-benzimidazol-2-ylthio)methyl]-2-pyridinamine hemihydrate, 1.9 ml (ca. 18 mmole) of 50% aqueous chloroacetaldehyde, and 1.5 g (18 mmole) of sodium bicarbonate in 25 ml of ethanol was stirred at room temperature. After three days the mixture was filtered and the filtrate was concentrated in vacuo. Trituration of the residue from the filtrate with a mixture of water and dichloromethane induced crystallization. The solid was collected, washed sequentially with water and dichloromethane, and air dried to yield 3.0 g of the title compound. Structure assignment was supported by the nmr and infrared spectra and by elemental analysis.

Analysis. Calcd. for $C_{15}H_{12}N_4S.1/4H_2O$: C, 63.24; H, 4.42; N, 19.67; S, 11.25. Found: C, 63.24; H, 4.12; N, 19.42; S, 11.49.

EXAMPLE 2

2-[(imidazo[1,2-a]pyridin-8-ylmethyl)sulfonyl]-1H-benzimidazole ⅛ hydrate

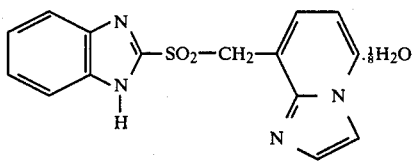

A suspension of 2.65 g (9 mmole) of 2-[(imidazo[1,2-a]pyridin-8-ylmethyl)thio]-1H-benzimidazole (see Example 1) in 50 ml of dichloromethane was cooled in an ice bath. A solution of 1.91 g (9 mmole) of ca. 85% m-chloroperbenzoic acid in the minimum amount of dichloromethane needed to form a solution was then added dropwise with stirring. The reaction was quenched with a few drops of dimethylsulfide. The mixture was washed with saturated aqueous sodium bicarbonate. The organic phase was concentrated in vacuo and chromatographed on silica gel (using ethanol-dichloromethane-triethylamine as eluent). Initial fractions yielded 326 mg of the title sulfone. Structure assignment was supported by the nmr and infrared spectra and by elemental analysis.

Analysis. Calcd. for $C_{15}H_{12}N_4SO_2 \cdot \frac{1}{8}H_2O$: C, 56.90; H, 3.90; N, 17.69; S, 10.12. Found: C, 56.84; H, 3.65; N, 17.64; S, 10.32.

EXAMPLE 3

2-[(imidazo[1,2-a]pyridin-8-ylmethyl)sulfinyl]-1H-benzimidazole ⅛ hydrate

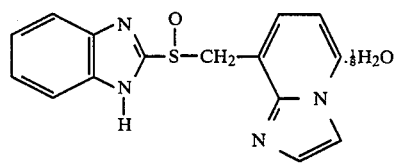

Later fractions from the chromatographic separation of Example 2 yielded 1.16 g of the title sulfoxide. Structure assignment was supported by the nmr and infrared spectra and by elemental analysis.

Analysis. Calcd. for $C_{15}H_{12}N_4SO \cdot \frac{1}{8}H_2O$: C, 59.93; H, 4.10; N, 18.64; S, 10.66. Found: C, 60.13; H, 4.00; N, 18.31; S, 10.45.

EXAMPLE 4

2-[[(2-methylimidazo[1,2-a]pyridin-8-yl)methyl]thio]-1H-benzimidazole

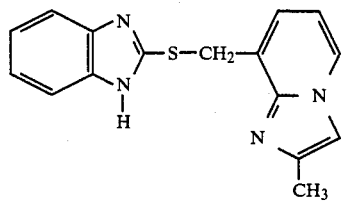

A mixture of 3.8 g (15 mmole) of 3-[(1H-benzimidazol-2-ylthio)methyl]-2-pyridinamine hemihydrate (see Example 1), 2.4 g (18 mmole) of bromoacetone, and 2.1 g (25 mmole) of sodium bicarbonate in 50 ml of ethanol was stirred at room temperature. After 18 hours the mixture was concentrated in vacuo to a residue that was partitioned between dilute hydrochloric acid and dichloromethane. The aqueous layer was made alkaline with potassium carbonate and extracted with dichloromethane. The organic layer was dried over magnesium sulfate, filtered, and concentrated in vacuo to an oil. Chromatography on basic alumina (using ethanol-toluene as eluent) yielded 1.6 g of the title compound. Structure assignment was supported by the nmr and infrared spectra.

EXAMPLE 5

2-[(2-methylimidazo[1,2-a]pyridin-8-yl)methyl]sulfinyl]-1H-benzimidazole

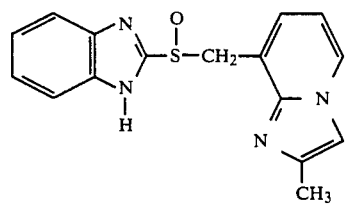

The title compound (117 mg) was prepared by the method of Example 2 using 1.24 g (4.2 mmole) of 2-[[(2-methylimidazo [1,2-a]pyridin-8-yl)methyl]thio]-1H-benzimidazole (see Example 4) instead of 2-[(imidazo[1,2-a]pyridin-8-ylmethyl)thio]-1H-benzimidazole. Structure assignment was supported by the nmr and infrared spectra and by elemental analysis.

Analysis. Calcd. for $C_{16}H_{14}N_4SO$: C, 61.92; H, 4.55; N, 18.05; S, 10.33. Found: C, 61.56; H, 4.68; N, 17.70; S, 9.98.

EXAMPLE 6

2-[(imidazo[1,2-a]pyridin-8-ylmethyl)thio]-5-methoxy-1H-benzimidazole

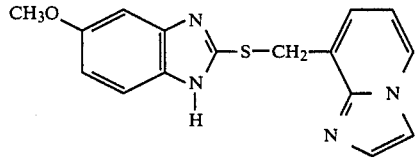

A mixture of 2.92 g (23 mmole) of 3-hydroxymethyl-2-pyridinamine, 6.15 g (35 mmole) of chloroacetaldehyde, and 2.0 g (35 mmole) of sodium bicarbonate in 100 ml of ethanol was heated at reflux for 1.5 hours. The mixture was filtered and the filtrate was concentrated in vacuo to a solid. Recrystallization from diethyl ether yielded 4.4 g of 8-hydroxymethylimidazo[1,2-a]pyridine, as confirmed by the nmr and infrared spectra. A mixture of 683 mg (3.8 mmole) of 2-mercapto-5-methoxybenzimidazole and 700 mg (3.8 mmole) of 8-hydroxymethylimidazo[1,2-a]pyridine was dissolved in 3 ml of 30% hydrogen bromide in acetic acid and heated on a steam bath. After being cooled to room temperature, the mixture was partitioned between 5% aqueous sodium hydroxide and dichloromethane. The organic layer was dried over sodium sulfate, filtered, and concentrated to yield the title compound as an oil. Structure assignment was supported by the nmr and infrared spectra.

EXAMPLE 7

2-[(imidazo[1,2-a]pyridin-8-ylmethyl)sulfinyl]-5-methoxy-1H-benzimidazole

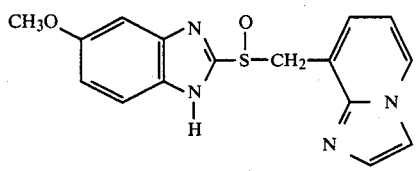

The title compound (71 mg) was prepared by the method of Example 2 using 2.7 g (9.6 mmole) of 2-[(imidazo[1,2-a]pyridin-8-ylmethyl)thio)-5-methoxy-1H-benzimidazole (see Example 6) instead of 2-[(imidazo[1,2-a]pyridin-8-ylmethyl)thio]-1H-benzimidazole. Structure assignment was supported by the nmr and infrared spectra and by elemental analysis.

Analysis. Calcd. for $C_{16}H_{14}N_4SO_2$: C, 58.88; H, 4.32; N, 17.17; S, 9.82. Found: C, 58.59; H, 4.22; N, 17.03; S, 9.69.

EXAMPLE 8

5-ethoxy-2-[(imidazo[1,2-a]pyridin-8-ylmethyl)thio]-1H-benzimidazole

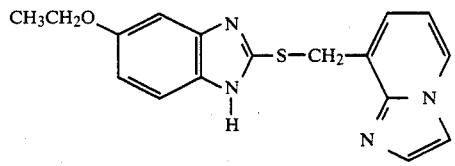

The title compound (573 mg), m.p. 157°–159.5°, was prepared by the method of Example 6 using 8-hydroxymethylimidazo[1,2-a]pyridine as the hydrochloride salt (1.0 g, 6.8 mmole) and using 1.3 g (6.8 mmole) of 5-ethoxy-2-mercaptobenzimidazole instead of 2-mercapto-5-methoxybenzimidazole. Structure assignment was supported by the nmr and infrared spectra and by elemental analysis.

Analysis. Calcd. for $C_{17}H_{16}N_4SO$: C, 62.92; H, 4.97; N, 17.27. Found: C, 62.76; H, 4.97; N, 17.03.

EXAMPLE 9

5-ethoxy-2-[(imidazo[1,2-a]pyridin-8-ylmethyl)sulfinyl]-1H-benzimidazole

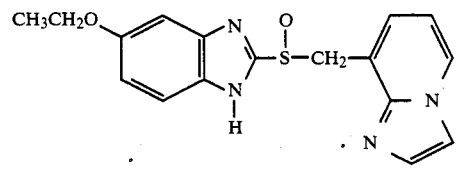

The title compound (161 mg), m.p. 186°–188°, was prepared by the method of Example 2 using 300 mg (1.54 mmole) of 5-ethoxy-2-[(imidazo[1,2-a]pyridin-8-ylmethyl)thio]-1H-benzimidazole (see Example 8) instead of 2-[(imidazo[1,2-a]pyridin-8-ylmethyl)thio]-1H-benzimidazole. Structure assignment was supported by the nmr and infrared spectra and by elemental analysis.

Analysis: Calcd. for $C_{17}H_{16}N_4SO_2$: C, 59.98; H, 4.74; N, 16.46; S, 9.42. Found: C, 59.77; H, 4.69; N, 16.55; S, 9.55.

EXAMPLE 10

2-[(imidazo[1,2-a]pyridin-8-ylmethyl)thio]-4-methyl-1H-benzimidazole

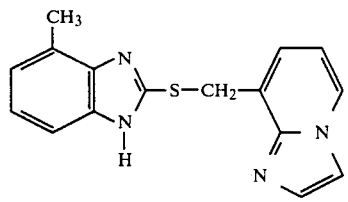

A solution of 20 g (0.13 mole) of 2-methyl-6-nitroaniline in 22.9 ml of concentrated aqueous hydrochloric acid, 200 ml of tetrahydrofuran, and 350 ml of methanol was hydrogenated at room temperature using 25 p.s.i. of hydrogen gas over 2.0 g of 5% palladium on carbon. The mixture was filtered and the filtrate was concentrated in vacuo. The residue was dissolved in 150 ml of ethanol and neutralized with 17.2 g (0.26 mole) of potassium hydroxide dissolved in 30 ml of water. Potassium ethylxanthate (23 g, 0.155 mole) was added and the mixture was heated at reflux for 18 hours. Upon cooling, a solid was collected, washed with water, and air dried to yield 6.2 g of 2-mercapto-4-methylbenzimidazole, as confirmed by the nmr and infrared spectra. The title compound (987 mg) was prepared by the method of Example 6 using 8-hydroxymethylimidazo[1,2-a]pyridine as the hydrochloride salt (700 mg, 3.8 mmole) and using 655 mg (4.0 mmole) of 2-mercapto-4-methylbenzimidazole instead of 2-mercapto-5-methoxybenzimidazole. Structure assignment was supported by the nmr and infrared spectra.

EXAMPLE 11

2-[(imidazo[1,2-a]pyridin-8-ylmethyl)sulfinyl]-4-methyl-1H-benzimidazole

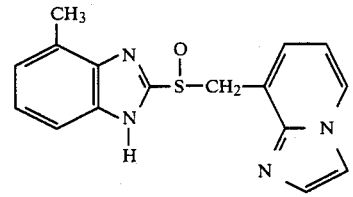

The title compound (481 mg), m.p. 166°–168°, was prepared by the method of Example 2 using 300 mg (1.54 mmole) of 2-[(imidazo[1,2-a]pyridin-8-ylmethyl)-thio]-4-methyl-1H-benzimidazole (see Example 10) instead of 2-[(imidazo[1,2-a]pyridin-8-ylmethyl)thio]-1H-benzimidazole. Structure assignment was supported by the nmr and infrared spectra and by elemental analysis.

Analysis. Calcd. for $C_{16}H_{14}N_4SO$: C, 61.92; H, 4.55; N, 18.05; S, 10.33. Found: C, 61.88; H, 4.58; N, 18.03; S, 10.47.

EXAMPLE 12

2-[(imidazo[1,2-a]pyridin-8-ylmethyl)thio]-5-methyl-1H-benzimidazole hemihydrate

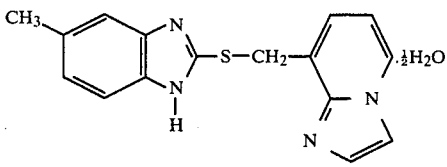

A mixture of 12.2 g (0.1 mole) of 3,4-diaminotoluene, 35 ml of carbon disulfide, and 4.0 g (0.1 mole) of sodium hydroxide was heated at reflux in 350 ml of ethanol. After 2.5 hours the mixture was concentrated in vacuo. The residue was suspended in 200 ml of 4% aqueous hydrochloric acid, collected by filtration, washed sequentially with water and diethyl ether, and air dried to yield 12.2 g of 2-mercapto-5-methylbenzimidazole, as confirmed by the nmr and infrared spectra. The title compound (796 mg) was prepared by the method of Example 6 using 8-hydroxymethylimidazo[1,2-a]pyridine as the hydrochloride salt and using 569 mg (3.5 mmole) of 2-mercapto-5-methylbenzimidazole instead of 2-mercapto-5-methoxybenzimidazole. Structure assignment was supported by elemental analysis.

Analysis Calcd. for $C_{16}H_{14}N_4S \cdot \frac{1}{2}H_2O$: C, 63.34; H, 4.94; N, 18.47; S, 10.57. Found: C, 63.86; H, 4.60; N, 18.87; S, 10.71.

EXAMPLE 13

2-[(imidazo[1,2-a]pyridin-8-ylmethyl)sulfinyl]-5-methyl-1H-benzimidazole

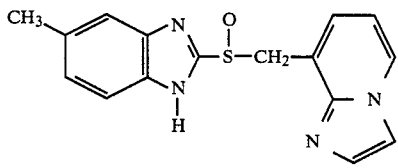

The title compound (445 mg) was prepared by the method of Example 2 using 700 mg (2.4 mmole) of 2-[(imidazo[1,2-a]pyridin-8-ylmethyl)thio]-5-methyl-1H-benzimidazole (see Example 12) instead of 2-[(imidazo[1,2-a]pyridin-8-ylmethyl)thio]-1H-benzimidazole. Structure assignment was supported by the nmr and infrared spectra and by elemental analysis.

Analysis Calcd. for $C_{16}H_{14}N_4SO$: C, 61.92; H, 4.55; N, 18.05; S, 10.33. Found: C, 62.43; H, 4.54; N, 18.18; S, 10.39.

EXAMPLE 14

2-[(imidazo[1,2-a]pyridin-8-ylmethyl)thio]-5,6-dimethyl-1H-benzimidazole

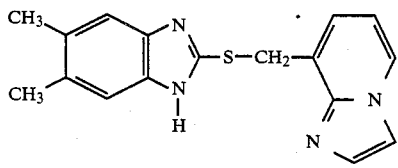

Reaction of 30 g (0.22 mole) of 4,5-dimethyl-1,2-phenylenediamine with potassium ethylxanthate using the method described in Example 10 yielded 19 g of 5,6-dimethyl-2-mercaptobenzimidazole, as confirmed by the nmr and infrared spectra and by elemental analysis. The title compound (591 mg) was prepared by the method of Example 6 using 8-hydroxymethylimidazo[1,2-a]pyridine as the hydrochloride salt and using 1.32 g (7.44 mmole) of 2-mercapto-4-methylbenzimidazole instead of 2-mercapto-5-methoxybenzimidazole. The compound was used in subsequent reactions without further characterization.

EXAMPLE 15

2-[(imidazo[1,2-a]pyridin-8-ylmethyl)sulfinyl]-5,6-dimethyl-1H-benzimidazole hydrate

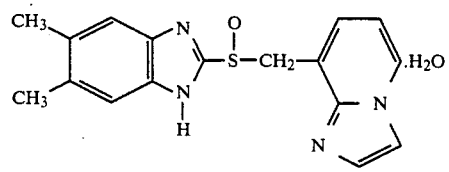

The title compound (167 mg) was prepared by the method of Example 2 using 550 mg (1.8 mmole) of 2-[(imidazo[1,2-a]pyridin-8-ylmethyl)thio]-5,6-dimethyl-1H-benzimidazole (see Example 14) instead of 2-[(imidazo[1,2-a]pyridin-8-ylmethyl)thio]-1H-benzimidazole. Structure assignment was supported by the nmr and infrared spectra and by elemental analysis.

Analysis Calcd. for $C_{17}H_{16}N_4SO_2 \cdot H_2O$: C, 59.63; H, 5.30; N, 16.36; S, 9.36. Found: C, 59.54; H, 5.21; N, 16.10; S, 8.97.

EXAMPLE 16

2-[(imidazo[1,2-a]pyridin-8-ylmethyl)thio]-5,6-dimethoxy-1H-benzimidazole

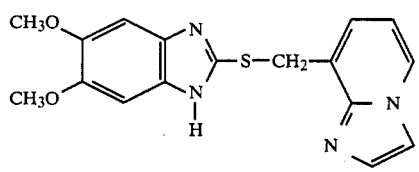

A solution of 62.2 g (0.31 mole) of 3,4-dimethoxy-6-nitroaniline in tetrahydrofuran was hydrogenated with Raney nickel to yield 52.7 g of the corresponding diamino compound. Reaction of the diamino compound with potassium ethylxanthate using the method described in Example 10 yielded 59 g of 5,6-dimethoxy-2-mercaptobenzimidazole as confirmed by the nmr and infrared spectra. The title compound (798 mg) was prepared by the method of Example 6 using 1.42 g (6.8 mmole) of 5-ethoxy-2-mercaptobenzimidazole instead of 2-mercapto-5-methoxybenzimidazole. Structure assignment was supported by the nmr and infrared spectra.

EXAMPLE 17

2-[(imidazo[1,2-a]pyridin-8-ylmethyl)sulfinyl]-5,6-dimethoxy-1H-benzimidazole

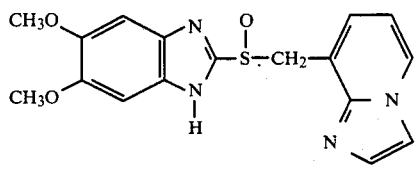

The title compound (126 mg), m.p. 195°-196°, was prepared by the method of Example 2 using 580 mg (1.71 mmole) of 2-[(imidazo[1,2-a]pyridin-8-ylmethyl)thio]-5,6-dimethoxy-1H-benzimidazole (see Example 16) instead of 2-[(imidazo[1,2-a]pyridin-8-ylmethyl)thio]-1H-benzimidazole. Structure assignment was supported by the nmr and infrared spectra and by elemental analysis.

Analysis. Calcd. for $C_{17}H_{16}N_4SO_3$: C, 57.29; H, 4.52; N, 15.72; S, 9.00. Found: C, 56.86; H, 4.44; N, 15.78; S, 8.96.

EXAMPLE 18

5-Chloro-2-[(imidazo[1,2-a]pyridin-8-ylmethyl)thio]-1H-benzimidazole

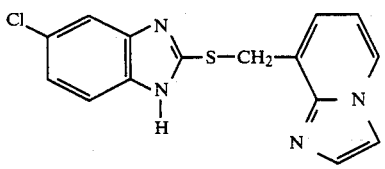

A solution of 20 g (0.12 mole) of 3-chloro-6-nitroaniline in 350 ml of methanol was hydrogenated over 5% palladium on carbon to yield 24.9 g of the corresponding diamino compound. Reaction of the diamino compound with potassium ethylxanthate using the method described in Example 10 yielded 19 g of 5-chloro-2-mercaptobenzimidazole, as confirmed by elemental analysis. The title compound (1.14 g) was prepared by the method of Example 6 using 8-hydroxymethylimidazo[1,2-a]pyridine as the hydrochloride salt (701 mg, 3.8 mmole) and using 701 mg (3.8 mmole) of 5-chloro-2-mercaptobenzimidazole instead of 2-mercapto-5-methoxybenzimidazole. Structure assignment was supported by the nmr and infrared spectra.

EXAMPLE 19

5-chloro-2-[(imidazo[1,2-a]pyridin-8-ylmethyl)sulfinyl]-1H-benzimidazole

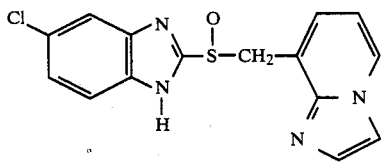

The title compound (343 mg) was prepared by the method of Example 2 using 1.04 g (3.3 mmole) of 5-chloro-2-[(imidazo[1,2-a]pyridin-8-ylmethyl)thio]-1H-benzimidazole (see Example 18) instead of 2-[(imidazo[1,2-a]pyridin-8-ylmethyl)thio]-1H-benzimidazole. Structure assignment was supported by the nmr and infrared spectra and by elemental analysis.

Analysis. Calcd. for $C_{15}H_{11}NCl_4SO$: C, 54.46; H, 3.35; N, 16.94; S, 9.69; Cl, 10.72. Found: C, 54.04; H, 3.42; N, 16.51; S, 9.20; Cl, 10.66.

EXAMPLE 20

2-[(imidazo[1,2-a]pyridin-8-ymethyl)thio]-5-(trifluoromethyl)-1H-benzimidazole hemihydrate

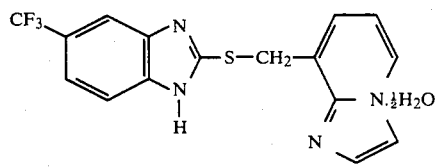

A solution of 50 g (0.24 mole) of 4-(trifluoromethyl)-2-nitroaniline in 500 ml of ethanol was hydrogenated over 10% palladium on carbon to yield 21.0 g of the corresponding diamino compound. Reaction of 20.0 g of the diamino compound with carbon disulfide using the method described in Example 12 yielded 22.9 g of 5-(trifluoromethyl)-2-mercaptobenzimidazole, as confirmed by elemental analysis. The title compound (654 mg) was prepared by the method of Example 6 using 8-hydroxymethylimidazo[1,2-a]-pyridine as the hydrochloride salt (700 mg, 3.8 mmole) and using 828 mg (3.8 mmole) of 2-mercapto-5-(trifluoromethyl)benzimidazole instead of 2-mercapto-5-methoxybenzimidazole. Structure assignment was supported by the nmr and infrared spectra and by elemental analysis.

Analysis. Calcd. for $C_{16}H_{11}N_4F_3S \cdot \frac{1}{2}H_2O$: C, 53.78; H, 3.10; N, 15.68; S, 8.97. Found: C, 53.86; H, 3.14; N, 15.70; S, 9.40.

EXAMPLE 21

2-[(imidazo[1,2-a]pyridin-8-ylmethyl)sulfinyl]-5-(trifluoromethyl)-1H-benzimidazole

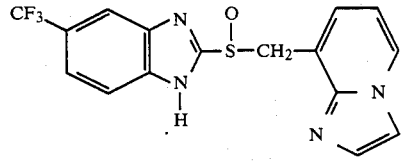

The title compound (294 mg) was prepared by the method of Example 2 using 616 mg (2.0 mmole) of 2-[(imidazo[1,2-a]pyridin-8-ylmethyl)thio]-5-(trifluoromethyl)-1H-benzimidazole (see Example 20) instead of 2-[(imidazo[1,2-a]pyridin-8-ylmethyl)thio]-1H-benzimidazole. Structure assignment was supported by the nmr and infrared spectra and by elemental analysis.

Analysis. Calcd. for $C_{16}H_{11}N_4F_3SO$: C, 52.75; H, 3.04; N, 15.38; S, 8.80; F, 15.64. Found: C, 51.49; H, 3.00; N, 15.13; S, 9.07; F, 15.42.

EXAMPLE 22

2-[[(2,3-dimethylimidazo[1,2-a]pyridin-8-yl)methyl]thio]-1H-benzimidazole

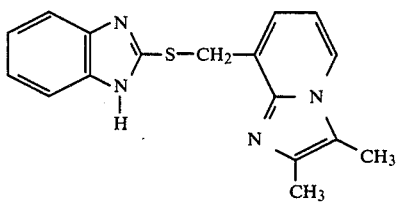

A mixture of 2.0 g (12 mmole) of 3-(acetoxymethyl)-2-pyridinamine, 1.7 g (17 mmole) of 3-chloro-2-butanone, and one crystal of potassium iodide was heated at 100° for 4.5 hours. The mixture was allowed to cool and was partitioned between aqueous potassium carbonate and dichloromethane. The organic phase was separated, washed with water, dried over magnesium sulfate, filtered, and concentrated in vacuo. The solid was triturated with diethyl ether and collected by filtration to yield 738 mg of 8-(acetoxymethyl)-2,3-dimethylimidazo[1,2-a]pyridine, as confirmed by the nmr and infrared spectra and by elemental analysis. [Calcd. for $C_{12}H_{14}N_2O_2$: C, 66.04; H, 6.47; N, 12.84. Found: C, 66.01; H, 6.38; N, 13.05.] A mixture of 700 mg (3.2 mmole) of 8-(acetoxymethyl)-2,3-dimethylimidazo[1,2-a]pyridine and 482 mg (3.2 mmole) of 2-mercaptobenzimidazole in 10 ml of 15% hydrogen bromide in acetic acid was heated on a steam bath. After being cooled to room temperature, the mixture was partitioned between 5% aqueous sodium hydroxide and dichloromethane. The organic layer was dried over sodium sulfate, filtered, and concentrated to an oil. Spinning disk chromatography on silica gel (using 1% by volume ethanol-dichloromethane as eluent) yielded 1.05 g of the title compound Structure assignment was supported by the nmr and infrared spectra.

EXAMPLE 23

2-[[(2,3-dimethylimidazo[1,2-a]pyridin-8-yl)methyl]sulfinyl]-1H-benzimidazole

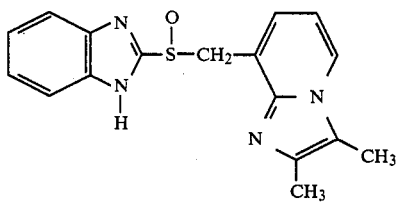

The title compound (242 mg) was prepared by the method of Example 2 using 990 mg (3.1 mmole) of 2-[[(2,3-dimethylimidazo[1,2-a]pyridin-8-yl)methyl]thio]-1H-benzimidazole (see Example 22) instead of 2-[(imidazo[1,2-a]pyridin-8-ylmethyl)thio]-1H-benzimidazole. Structure assignment was supported by the nmr and infrared spectra and by elemental analysis.

Analysis. Calcd. for $C_{17}H_{16}N_4SO$: C, 62.50; H, 5.01; N, 17.15; S, 9.81. Found: C, 62.30; H, 4.68; N, 16.85; S, 9.86.

EXAMPLE 24

2-[[(3-methylimidazo[1,2-a]pyridin-8-yl)methyl]thio]-1H-benzimidazole

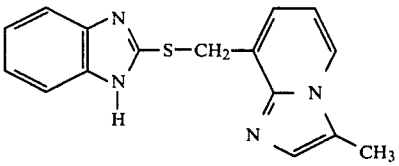

A mixture of 5.0 g (30 mmole) of 3-(acetoxymethyl)-2-pyridinamine and 4.8 g (35 mmole) of 2-bromopropanal spontaneously heated upon mixing. After cooling, the mixture was partitioned between aqueous potassium carbonate and dichloromethane. The organic phase was separated, washed with water, dried over magnesium sulfate, filtered, and concentrated in vacuo. Chromatography on silica gel (using ethanol-dichloromethane as eluent) yielded 2.3 g of 8-(acetoxymethyl)-3-methylimidazo[1,2-a]pyridine, as confirmed by the nmr and infrared spectra and by elemental analysis. [Calcd. for $C_{11}H_{12}N_2O_2$: C, 64.69; H, 5.92; N, 13.72. Found: C, 63.70; H, 5.85; N, 14.24). A mixture of 2.3 g (11 mmole) of 8-(acetoxymethyl)-3-methylimidazo[1,2-a]pyridine and 1.65 g (11 mmole) of 2-mercaptobenzimidazole in 40 ml of 15% hydrogen bromide in acetic acid was heated on a steam bath. After being cooled to room temperature, the mixture was partitioned between 5% aqueous sodium hydroxide and dichloromethane. The organic layer was dried over sodium sulfate, filtered, and concentrated to an oil. Chromatography yielded 2.1 g of the title compound. Structure assignment was supported by the nmr and infrared spectra.

EXAMPLE 25

2-[[(3-methylimidazo[1,2-a]pyridin-8-yl)methyl]sulfinyl]-1H-benzimidazole hemihydrate·¼CH$_2$Cl$_2$

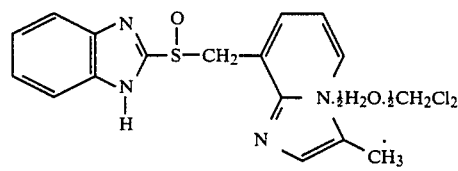

The title compound (831 mg) was prepared by the method of Example 2 using 2.0 g (6.8 mmole) of 2-[[(3-methylimidazo[1,2a]pyridin-8-yl)methyl]thio]-1H-benzimidazole (see Example 24) instead of 2-[(imidazo[1,2-a]pyridin-8-ylmethyl)thio]-1H-benzimidazole. Structure assignment was supported by the nmr and infrared spectra and by elemental analysis.

Analysis. Calcd. for $C_{16}H_{14}N_4SO·½H_2O·¼CH_2Cl_2$: C, 58.68; H, 4.65; N, 16.78; S, 9.71. Found: C, 58.70; H, 4.31; N, 17.32; S, 9.89.

EXAMPLE 26

2-[[(2-phenylimidazo[1,2-a]pyridin-8-yl)methyl]thio]-1H-benzimidazole

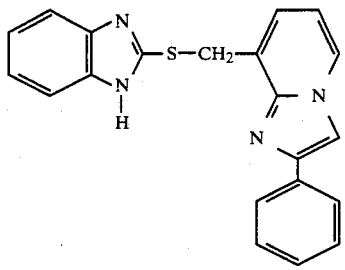

A mixture of 1.24 g (10 mmole) of 3-hydroxymethyl-2-pyridinamine and 2.0 g (10 mmole) of α-bromoacetophenone in 25 ml of ethanol was stirred at room temperature. After 18 hours the resultant solid was collected, washed with ethano, and dissolved in water. The solution was made basic with aqueous potassium carbonate and extracted with dichloromethane. The organic layer was dried over magnesium sulfate, filtered, and concentrated in vacuo. The residue was triturated with diethyl ether, collected by filtration, washed with diethyl ether, and air dried to yield 1.4 g of 8-hydroxymethyl-2-phenylimidazo[1,2-a]pyridine, as confirmed by the nmr and infrared spectra and by elemental analysis. [Calcd. for $C_{14}H_{12}N_2O_2$: C, 74.98; H, 5.39; N, 12.49. Found: C, 74.68; H, 5.39; N, 12.40.] A mixture of 871 mg (5.8 mmole) of 2-mercaptobenzimidazole and 1.3 g (5.8 mmole) of 8-hydroxymethyl-2-phenylimidazo[1,2-a]pyridine was dissolved in 10 ml of 47% aqueous hydrobromic acid and 10 ml of acetic acid and heated to reflux. After being cooled to room temperature, the mixture was poured into water, made alkaline with potassium carbonate, and extracted with dichloromethane. The organic layer was dried over magnesium sulfate, filtered, and concentrated in vacuo. Trituration of the residue with diethyl ether yielded 1.8 g of the analytically pure title compound. Structure assignment was supported by the nmr and infrared spectra and by elemental analysis.

Analysis. Calcd. for $C_{21}H_{16}N_4S$: C, 70.76; H, 4.52; N, 15.72; S, 8.99. Found: C, 70.42; H, 4.68; N, 15.66; S, 8.88.

EXAMPLE 27

[[2-phenylimidazo[1,2-a]pyridin-8-yl)methyl]sulfonyl]-1H-benzimidazole¼hydrate

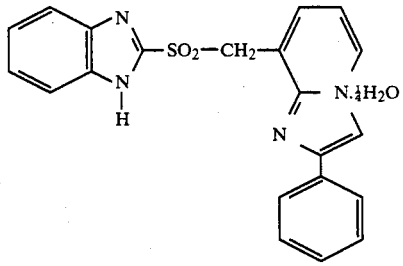

The title sulfone (121 mg) was prepared by the method of Example 2 using 1.2 g (3.4 mmole) of 2-[[(2-phenylimidazo[1,2-a]pyridin-8-yl)methyl]thio]-1H-benzimidazole (see Example 26) instead of 2-[(imidazo[1,2-a]pyridin-8-ylmethyl)thio]-1H-benzimidazole and using ethanol-toluene as chromatography eluent instead of ethanol-dichloromethane-triethylamine. Initial chromatographic fractions contained the sulfone. Structure assignment was supported by the nmr and infrared spectra and by elemental analysis.

Analysis. Calcd. for $C_{21}H_{16}N_4SO_2.\frac{1}{4}H_2O$: C, 64.18; H, 4.23; N, 14.26; S, 8.16. Found: C, 63.95; H, 4.18; N, 14.29; S, 8.33.

EXAMPLE 28

2-[[(2-phenylimidazo[1,2-a]pyridin-8-yl)methyl]sulfinyl]-1H-benzimidazole ¼ hydrate

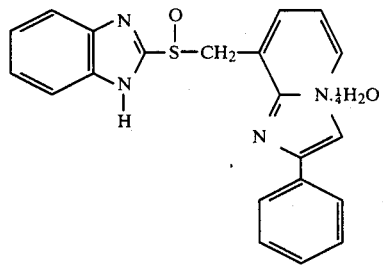

Later fractions from the chromatographic separation of Example 27 yielded 380 mg of the title sulfoxide as the ¼ hydrate. Structure assignment was supported by the nmr and infrared spectra and by elemental analysis.

Analysis. Calcd. for $C_{21}H_{16}N_4SO.\frac{1}{4}H_2O$: C, 66.91; H, 4.41; N, 14.86; S, 8.50. Found: C, 66.64; H, 4.44; N, 14.79; S, 8.52.

EXAMPLE 29

2-[[(3-phenylimidazo[1,2-a]pyridin-8-yl)methyl]thio]-1H-benzimidazole

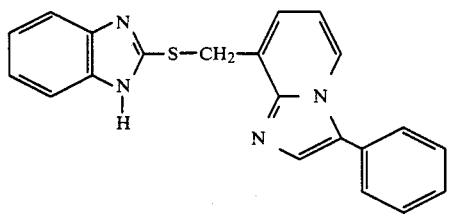

A mixture of 4.4 g (26 mmole) of 3-(acetoxymethyl)-2-pyridinamine and 6.0 g (30 mmole) of 2-bromo-2-phenylacetaldehyde was heated at 65°. The mixture was dissolved in water, made basic with aqueous potassium carbonate, and extracted with dichloromethane. The organic layer was washed with water, dried over magnesium sulfate, filtered, and concentrated in vacuo. The residue was triturated with diethyl ether to yield 4.1 g of 8-(acetoxymethyl)-3-phenylimidazo[1,2-a]pyridine as confirmed by the nmr and infrared spectra and by elemental analysis. [Calcd. for $C_{16}H_{14}N_2O_2$: C, 72.17; H, 5.30; N, 10.52. Found: C, 71.90; H, 5.25; N, 10.43.] The title compound (1.5 g) was prepared by the method described in Example 26 using 1.3 g (5 mmole) of 8-(acetoxymethyl)-3-phenylimidazo[1,2-a]pyridine instead of 8-hydroxymethyl-2-phenylimidazo[1,2-a]pyridine. Structure assignment was supported by the nmr and infrared spectra and by elemental analysis.

Analysis. Calcd. for $C_{21}H_{16}N_4S$: C, 70.76; H, 4.52; N, 15.72; S, 8.99. Found: C, 70.06; H, 4.46; N, 15.55; S, 9.11.

EXAMPLE 20

2-[[(3-phenylimidazo[1,2-a]pyridin-8-yl)methyl]sulfinyl]-1H-benzimidazole hemihydrate

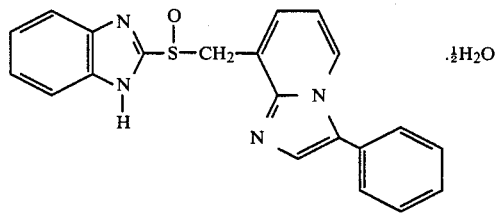

The title compound (1.2 g) was prepared by the method of Example 2 using 1.5 g (4.2 mmole) of 2-[[(3-phenylimidazo[1,2-a]pyridin-8-yl)methyl]thio]-1H-benzimidazole (see Example 29) instead of 2-[(imidazo[1,2-a]pyridin-8-ylmethyl)thio]-1H-benzimidazole. Structure assignment was supported by the nmr and infrared spectra and by elemental analysis.

Analysis. Calcd. for $C_{21}H_{16}N_4SO.\frac{1}{2}H_2O$: C, 66.12; H, 4.49; N, 14.68; S, 8.40. Found: C, 66.48; H, 4.23; N, 15.08; S, 8.67.

EXAMPLE 31

2-[[[3-(4-nitrophenyl)imidazo[1,2-a]pyridin-8-yl]methyl]thio]-1H-benzimidazole hydrate

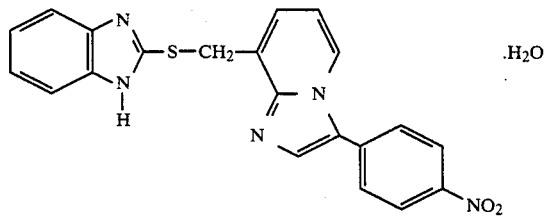

A mixture of 16.0 g (80 mmole) of 1-bromo-4-nitrobenzene, 11.2 ml (ca. 120 mmole) of ethyl vinyl ether, 179.2 mg of lead(II) acetate, 484 mg of tri-o-tolylphosphine, and 22 ml (ca. 160 mmole) of triethylamine was placed in a bomb, purged with nitrogen, and heated at 100° for eight hours. The reaction mixture was partitioned between diethyl ether and water and clarified by filtration. The organic layer was washed with water, dried over magnesium sulfate, filtered, and concentrated in vacuo. Chromatography of the residue on silica gel (using toluene-hexane as eluant) yielded three principle components (in order of elution): 2.1 g of 4-(1-ethoxyvinyl)nitrobenzene, 3.0 g of the cis isomer of 4-(2-ethoxyviny)nitrobenzene, and 7.2 g of the trans isomer of 4-(2-ethoxyvinyl)nitrobenzene. A solution of 3.0 g (15 mmole) of 4-(2-ethoxyvinyl)nitrobenzene (as a mixture of cis and trans isomers) in 30 ml of diethyl ether was cooled to −15°. Bromine (2.48 ml, ca. 15 mmole) was added dropwise as the temperature was maintained at or below −10°. The reaction mixture was poured into 50 ml of water containing 5 g of sodium bicarbonate. After two hours of stirring, the mixture was allowed to separate into layers. The organic layer was washed with water, dried over sodium sulfate, filtered, and concentrated in vacuo to yield 3.9 g of 2-bromo-2-(4-nitrophenyl)acetaldehyde as an oil. A mixture of 1.98 g (15 mmole) of 3-hydroxymethyl-2-pyridinamine and 3.9 g (15 mmole) of 2-bromo-2-(4-nitrophenyl)acetaldehyde was warmed to initiate an exothermic reactiion. After cooling, the mixture was shaken with aqueous potassium carbonate and dichloromethane. The solid was collected, washed with water and dichloromethane, and air dried to yield 2.84 g of 8-hydroxymethyl-2-(4-nitrophenyl)imidazo[1,2-a]pyridine, as confirmed by the nmr and infrared spectra. The title compound (100 mg) was prepared by the method described in Example 6 using 1.4 g (5.2 mmole) of 8-hydroxymethyl-2-(4-nitrophenyl)imidazo[1,2-a]pyridine instead of 8-hydroxymethylimidazo[1,2-a]pyridine. Structure assignment was supported by the nmr and infrared spectra and by elemental analysis.

Analysis. Calcd. for $C_{21}H_{15}N_5SO_2.H_2O$: C, 60.13; H, 4.08; N, 16.70. Found: C, 60.33; H, 3.71; N, 16.91.

EXAMPLE 32

2-[[[3-(4-nitrophenyl)imidazo[1,2-a]pyridin-8-yl]methyl]sulfonyl]-1H-benzimidazole

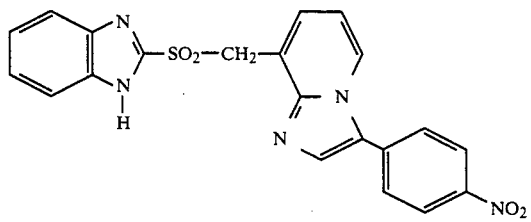

The title sulfone (103 mg) was prepared by the method of Example 2 using 650 mg (3.4 mmole) of 2-[[[3-(4-nitrophenyl)-imidazo[1,2-a]pyridin-8-yl]methyl]thio]-1H-benzimidazole hydrate (see Example 31) instead of 2-[(imidazo[1,2-a]pyridin-8-ylmethyl)thio]-1H-benzimidazole. Initial chromatographic fractions contained the sulfone. Structure assignment was supported by the nmr and infrared spectra and by elemental analysis.

Analysis. Calcd. for $C_{21}H_{15}N_5SO_4$: C, 58.18; H, 3.49; N, 16.16; S, 7.40. Found: C, 57.78; H, 3.55; N, 16.03; S, 7.42.

EXAMPLE 33

2-[[[3-(4-nitrophenyl)imidazo[1,2-a]pyridin-8-yl]methyl]sulfinyl]-1H-benzimidazole ¼ hydrate

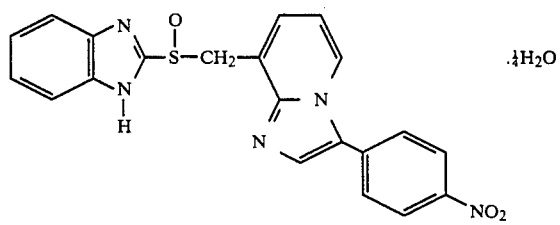

Later fractions from the chromatographic separation of Example 32 yielded 329 mg of the title sulfoxide as the ¼ hydrate. Structure assignment was supported by the nmr and infrared spectra and by elemental analysis.

Analysis. Calcd. for $C_{21}H_{15}N_5SO_3.\frac{1}{4}H_2O$: C, 59.77; H, 3.70; N, 16.59; S, 7.59. Found: C, 59.45; H, 3.78; N, 16.37; S, 7.49.

EXAMPLE 34

2-[[[3-[3-(trifluoromethyl)phenyl]imidazo[1,2-a]pyridin-8-yl]methyl]thio]-1H-benzimidazole ¼ diethyl ether solvate

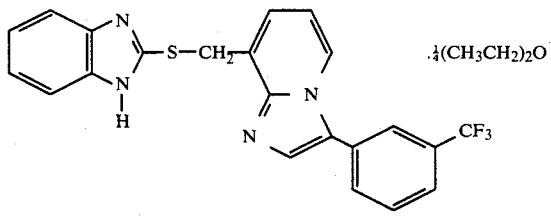

The title compound (1.2 g) was prepared by the method of Example 31 using 18 g (80 mmole) of 3-bromo-α,α,α-trifluorotoluene instead of 1-bromo-4-nitrobenzene and using triphenylphosphine instead of tri-o-tolylphosphine. Structure assignment was supported by the nmr and infrared spectra and by elemental analysis.

Analysis. Calcd. for $C_{22}H_{15}N_4F_3S.\frac{1}{4}(CH_3CH_2)_2O$: C, 61.31; H, 4.09; N, 13.00; S, 7.34. Found: C, 61.17; H, 4.71; N, 12.76; S, 7.76.

EXAMPLE 35

2-[[[3-[3-(trifluoromethyl)phenyl]imidazo[1,2-a]pyridin-8-yl]methyl]sulfonyl]-1H-benzimidazole

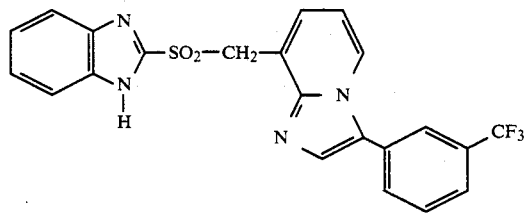

The title sulfone (46 mg) was prepared by the method of Example 2 using 985 mg (2.4 mmole) of 2-[[[3-[3-(trifluoromethyl)phenyl]imidazo[1,2-a]pyridin-8-yl]methyl)thio]-1H-benzimidazole ¼ diethyl ether solvate (see Example 34) instead of 2-[(imidazo[1,2-a]pyridin-8-ylmethyl)thio]-1H-benzimidazole. Initial chromatographic fractions contained the sulfone. Structure assignment was supported by the nmr and infrared spectra and by elemental analysis.

Analysis. Calcd. for $C_{22}H_{15}N_4F_3SO_2$: C, 57.89; H, 3.31; N, 12.27; S, 7.02. Found: C, 57.57; H, 3.32; N, 12.06; S, 7.31.

EXAMPLE 36

2-[[[3-[3-(trifluoromethyl)phenyl]imidazo[1,2-a]pyridin-8-yl]methyl]sulfinyl]-1H-benzimidazole

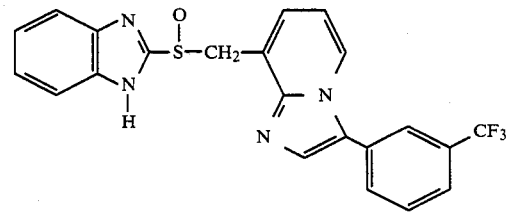

Later fractions from the chromatographic separation of Example 35 yielded 667 mg of the title sulfoxide. Structure assignment was supported by the nmr and infrared spectra and by elemental analysis.

Analysis. Calcd. for $C_{22}H_{15}N_4FSO$: C, 59.99; H, 3.43; N, 12.72; S, 7.27. Found: C, 59.70; H, 3.49; N, 12.73; S, 7.53.

EXAMPLE 37

5-methyl-2-[[[3-[3-(trifluoromethyl)phenyl]imidazo[1,2-a]pyridin-8-yl]methyl]thio]-1H-benzimidazole ¼ diethyl ether solvate

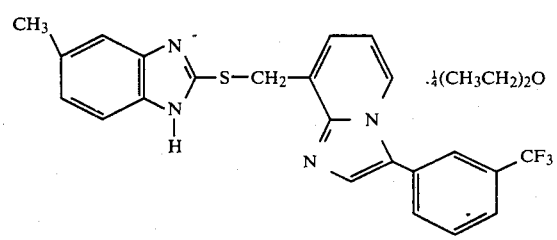

The title compound (1.28 g) was prepared by the methods described in Examples 34 and 6 using 562 mg (3.4 mmole) of 2-mercapto-5-methylbenzimidazole instead of 2-mercapto-5-methoxybenzimidazole. Structure assignment was supported by the nmr and infrared spectra and by elemental analysis.

Analysis. Calcd. for $C_{23}H_{17}N_4F_3S.\frac{1}{4}(CH_3CH_2)_2O$: C, 62.09; H, 4.41; N, 12.59; S, 7.20; F, 12.80. Found: C, 62.49; H, 3.92; N, 12.71; S, 7.52; F, 12.65.

EXAMPLE 28

5-methyl-2-[[[3-[3-(trifluoromethyl)phenyl]imidazo[1,2-a]pyridin-8-yl]methyl]sulfonyl]-1H-benzimidazole

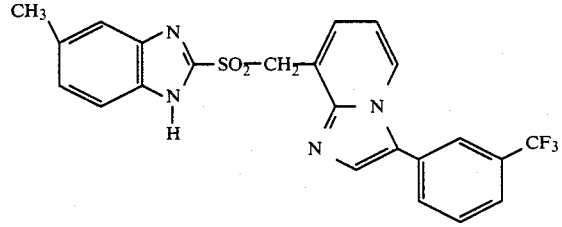

The title sulfone (87 mg) was prepared by the method of Example 2 using 1.0 g (3.4 mmole) of 5-methyl-2-[[[3-[3-(trifluoromethyl)phenyl]imidazo[1,2-a]pyridin-8-yl]methyllthio]-1H-benzimidazole ¼ diethyl ether solvate (see Example 37) instead of 2-[(imidazo[1,2-a]pyridin-8-ylmethyl)thio]-1H-benzimidazole. Initial chromatographic fractions contained the sulfone. Structure assignment was supported by the nmr and infrared spectra and by elemental analysis.

Analysis. Calcd. for $C_{23}H_{17}N_4F_3SO_2$: C, 58.71; H, 3.64; N, 11.81; S, 6.81. Found: C, 58.26; H, 3.60; N, 11.81; S, 6.96.

EXAMPLE 39

5-methyl-2-[[[3-[3-(trifluoromethyl)phenyl]imidazo[1,2-a]pyridin-8-yl]methyl]sulfinyl]-1H-benzimidazole

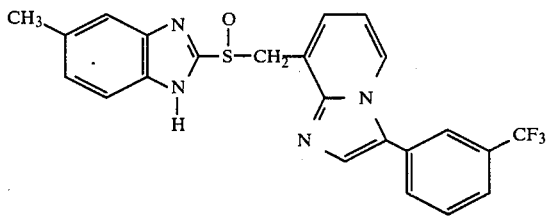

Later fractions from the chromatographic separation of Example 38 yielded 853 mg of the title sulfoxide. Structure assignment was supported by the nmr and infrared spectra and by elemental analysis.

Analysis. Calcd. for $C_{23}H_{17}N_4FSO$: C, 60.78; H, 3.77; N, 12.33; S, 7.05. Found: C, 60.60; H, 3.80; N, 12.35; S, 7.16.

EXAMPLE 40

5-chloro-2-[[[3-[3-(trifluoromethyl)phenyl]imidazo[1,2-a]pyridin-8-yl]methyl]thio]-1H-benzimidazole ¼ diethyl ether solvate

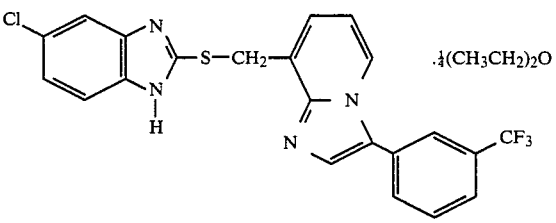

The title compound (1.06 g) was prepared by the methods described in Examples 34 and 6 using 631 mg (3.4 mmole) of 5-chloro-2-mercatobenzimidazole instead of 2-mercapto-5-methoxybenzimidazole. Structure assignment was supported by the nmr and infrared spectra and by elemental analysis.

Analysis. Calcd. for $C_{22}H_{14}N_4ClF_3S.\frac{1}{4}(CH_3CH_2)_2O$: C, 56.77; H, 3.57; N, 12.04; S, 7.61; F, 12.24. Found: C, 57.64; H, 3.31; N, 11.86; S, 7.34; F, 11.93.

EXAMPLE 41

5-chloro-2-[[[3-[3-(trifluoromethyl)phenyl]imidazo[1,2-a]pyridin-8-yl]methyl]sulfonyl]-1H-benzimidazole

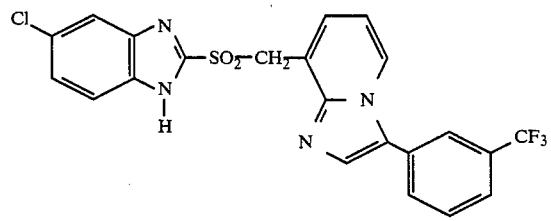

The title sulfone (86 mg) was prepared by the method of Example 2 using 806 mg (1.8 mmole) of 5-chloro-2-[[[3-[3-(trifluoromethyl)-phenyl]imidazo[1,2-a]pyridin-8-yl]methyl]thio]-1H-benzimidazole ¼ diethyl ether solvate (see Example 40) instead of 2-[(imidazo[1,2-a]pyridin-8-ylmethyl)thio]-1H-benzimidazole. Initial chromatographic fractions contained the sulfone. Structure assignment was supported by the nmr and infrared spectra and by elemental analysis.

Analysis. Calcd. for $C_{22}H_{14}N_4ClF_3SO_2$: C, 53.82; H, 2.87; N, 11.41; S, 6.53; Cl, 7.22. Found: C, 53.65; H, 2.81; N, 11.25; S, 6.82; Cl, 7.26.

EXAMPLE 42

5-chloro-2-[[[3-[3-(trifluoromethyl)phenyl]imidazo[1,2-a]pyridin-8-yl]methyl]sulfinyl]-1H-benzimidazole

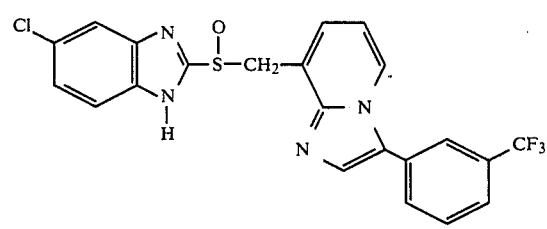

Later fractions from the chromatographic separation of Example 40 yielded 626 mg of the title sulfoxide. Structure assignment was supported by the nmr and infrared spectra and by elemental analysis.

Analysis. Calcd. for $C_{22}H_{14}N_4ClFSO$: C, 55.64; H, 2.97; N, 11.80; S, 6.75; Cl, 7.46. Found: C, 55.45; H, 2.86; N, 11.84; S, 6.88; Cl, 7.49.

EXAMPLE 43

2-[[[3-[4-(trifluoromethyl)phenyl]imidazo[1,2-a]pyridin-8-yl]methyl]thio]-1H-benzimidazole ⅛ diethyl ether ¼ dichloromethane solvate

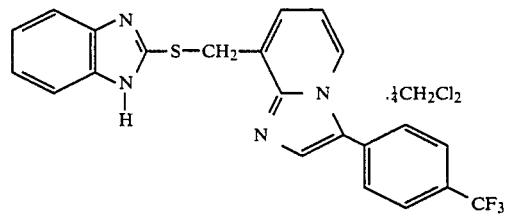

The title compound (1.02 g) was prepared by the method of Example 31 using 9 g (400 mmole) of 4-bromo-α,α,α-trifluorotoluene instead of 1-bromo-4-nitrobenzene and using triphenylphosphine instead of tri-o-tolylphosphine. Structure assignment was supported by the nmr and infrared spectra and by elemental analysis.

Analysis. Calcd. for $C_{21}H_{15}N_4F_3S.\frac{1}{8}(CH_3CH_2)_2O.\frac{1}{4}CH_2Cl_2$: C, 60.18; H, 3.89; N, 12.91; S, 7.38; F, 13.12. Found: C, 60.47; H, 3.60; N, 12.82; S, 7.65; F, 12.67.

EXAMPLE 44

2-[[[3-[4-(trifluoromethyl)phenyl]imidazo[1,2-a]pyridin-8-yl]methyl]sulfonyl]-1H-benzimidazole

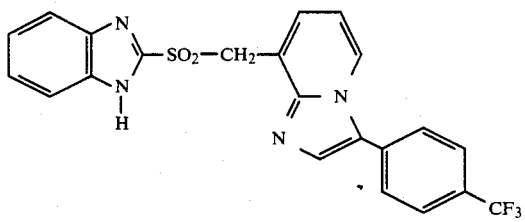

The title sulfone (118 mg) was prepared by the method of Example 2 using 774 mg (1.9 mmole) of 2-[[[3-[4-(trifluoromethyl)phenyl]imidazo[1,2-a]pyridin-8-yl]methyl]thio]-1H-benzimidazole ⅛ diethyl ether ¼ dichloromethane solvate (see Example 43) instead of 2-[(imidazo[1,2-a]pyridin-8-ylmethyl)thio]-1H-benzimidazole. Initial chromatographic fractions contained the sulfone. Structure assignment was supported by the nmr and infrared spectra and by elemental analysis.

Analysis. Calcd. for $C_{21}H_{15}N_4F_3SO_2$: C, 57.89; H, 3.31; N, 12.27; S, 7.02. Found: C, 57.70; H, 3.39; N, 12.07; S, 7.11.

EXAMPLE 45

2-[[[3-[4-(trifluoromethyl)phenyl]imidazo[1,2-a]pyridin-8-yl]methyl]sulfinyl]-1H-benzimidazole

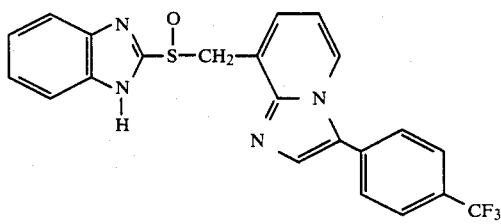

Later fractions from the chromatographic separation of Example 44 yielded 522 mg of the title sulfoxide. Structure assignment was supported by the nmr and infrared spectra and by elemental analysis.

Analysis. Calcd. for $C_{21}H_{15}N_4FSO$: C, 59.99; H, 3.43; N, 12.72; S, 7.27. Found: C, 59.93; H, 3.41; N, 12.72; S, 7.40.

EXAMPLE 46

5-chloro-2-[[[3-[4-(trifluoromethyl)phenyl]imidazo[1,2-a]pyridin-8-yl]methyl]thio]-1H-benzimidazole

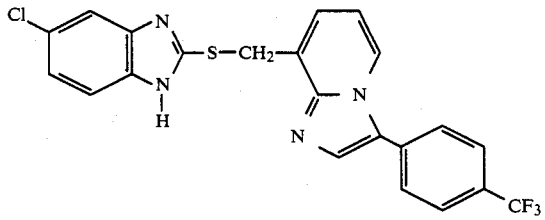

The title compound (1.06 g) was prepared by the methods described in Examples 43 and 6 using 950 mg (3.2 mmole) of 5-chloro-2-mercaptobenzimidazole instead of 2-mercapto-5-methoxybenzimidazole. Structure assignment was supported by the nmr and infrared spectra and by elemental analysis. Analysis. Calcd. for $C_{22}H_{14}N_4ClF_3S$: C, 56.44; H, 3.16; N, 12.52; S, 7.18; Cl, 7.93; F, 12.75. Found: C, 57.02; H, 3.11; N, 12.18; S, 7.18; Cl, 8.19; F, 12.13.

EXAMPLE 47

5-chloro-2-[[[3-[4-(trifluoromethyl)phenyl]imidazo[1,2-a]pyridin-8-yl]methyl]sulfinyl]-1H-benzimidazole

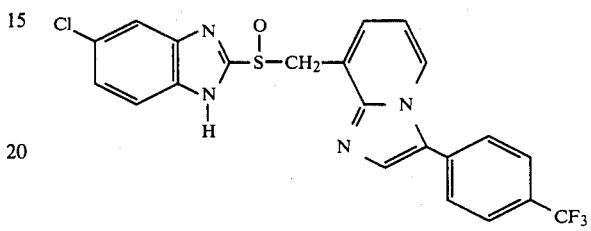

The title compound (577 mg) was prepared by the method of Example 2 using 838 mg (1.9 mmole) of 5-chloro-2-[[[3-[4-(trifluoromethyl)phenyl]imidazo[1,2-a]pyridin-8-yl]methyl]thio]-1H-benzimidazole (see Example 46) instead of 2-[(imidazo[1,2-a]pyridin-8-ylmethyl)thio]-1H-benzimidazole. Structure assignment was supported by the nmr and infrared spectra and by elemental analysis.

Analysis. Calcd. for $C_{22}H_{14}N_4ClF_3SO$: C, 54.49; H, 3.05; N, 12.10; S, 6.93; Cl, 7.66. Found: C, 54.39; H, 2.93; N, 11.79; S, 6.96; Cl, 7.49.

EXAMPLE 48 methyl 4-[8-[(1H-benzimidazol-2-ylthio)methyl]imidazo[1,2-a]pyridin-3-yl]benzoate

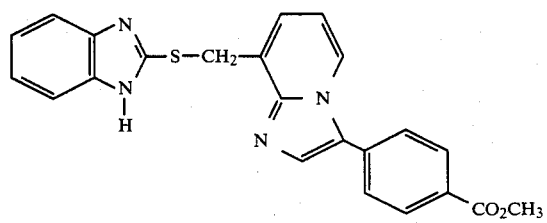

The title compound (200 mg) was prepared by the method of Example 31 using 10.4 g (40 mmole) of methyl 4-iodobenzoate instead of 1-bromo-4-nitrobenzene and using triphenylphosphine instead of tri-o-tolylphosphine. The title compound was used in subsequent reactions without further characterization.

EXAMPLE 49 methyl 4-[8-[(1H-benzimidazol-2-ylsulfinyl)methyl]imidazo[1,2-a]pyridin-3-yl]benzoate hydrate

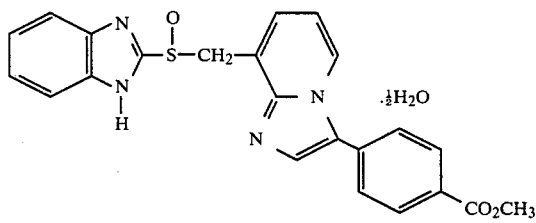

The title compound (75 mg) was prepared by the method of Example 2 using 200 mg (0.48 mmole) of methyl 4-[8-[(1H-benzimidazol-2-ylthio)methyl]imidazo[1,2-a]pyridin-3-yl]benzoate (see Example 48) instead of 2-[(imidazo[1,2-a]pyridin-8-ylmethyl)thio]-1H-benzimidazole. Structure assignment was supported by the nmr and infrared spectra and by elemental analysis.

Analysis. Calcd. for $C_{23}H_{18}N_4SO_3 \cdot H_2O$: C, 61.59; H, 4.49; N, 12.49; S, 7.14. Found: C, 61.97; H, 4.43; N, 12.31; S, 6.97.

EXAMPLE 50

2-[[[3-(4-chlorophenyl)imidazo[1,2-a]pyridin-8-yl]methyl]thio]-1H-benzimidazole

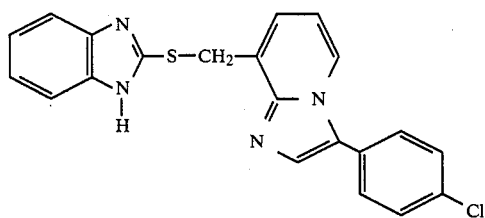

The title compound (1.0 g) was prepared by the method of Example 31 using 7.6 g (40 mmole) of 4-bromochlorobenzene instead of 1-bromo-4-nitrobenzene and using triphenylphosphine instead of tri-o-tolylphosphine. Structure assignment was supported by the nmr and infrared spectra and by elemental analysis.

Analysis. Calcd. for $C_{21}H_{15}N_4ClS$: C, 64.53; H, 3.87; N, 14.33; S, 8.20; Cl, 9.07. Found: C, 64.51; H, 3.84; N, 14.73; S, 8.31; Cl, 9.04.

EXAMPLE 51

2-[[[3-(4-chlorophenyl)imidazo[1,2-a]pyridin-8-yl]methyl]sulfonyl]-1H-benzimidazole

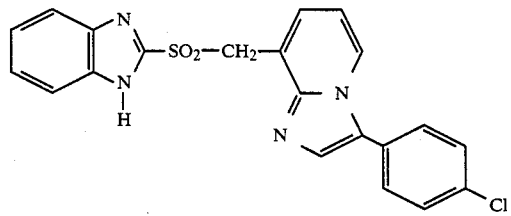

The title sulfone (95 mg) was prepared by the method of Example 2 using 900 mg (2.3 mmole) of 2-[[[3-(4-chlorophenyl)imidazo[1,2-a]pyridin-8-ylmethyl]thio]-1H-benzimidazole (see Example 50) instead of 2-[(imidazo[1,2-a]pyridin-8-ylmethyl)thio]-1H-benzimidazole. Initial chromatographic fractions contained the sulfone. Structure assignment was supported by the nmr and infrared spectra and by elemental analysis.

Analysis. Calcd. for $C_{21}H_{15}N_4ClSO_2$: C, 59.64; H, 3.58; N, 13.25; S, 7.58; Cl, 8.38. Found: C, 59.56; H, 3.42; N, 13.25; S, 7.56; Cl, 8.28.

EXAMPLE 52

2-[[[3-(4-chlorophenyl)imidazo[1,2-a]pyridin-8-yl]methyl]sulfinyl]-1H-benzimidazole

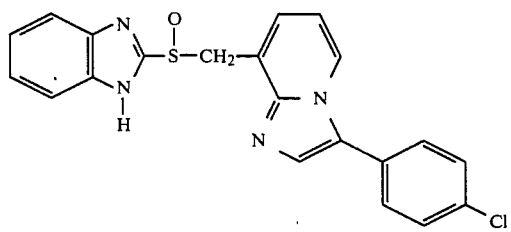

Later fractions from the chromatographic separation of Example 51 yielded 514 mg of the title sulfoxide. Structure assignment was supported by the nmr and infrared spectra and by elemental analysis.

Analysis. Calcd. for $C_{21}H_{15}N_4ClSO$: C, 61.99; H, 3.72; N, 13.77; S, 7.88; Cl, 8.71. Found: C, 61.78; H, 3.72; N, 13.65; S, 7.86; Cl, 8.78.

EXAMPLE 53

2-[[[3-(4-methylphenyl)imidazo[1,2-a]pyridin-8-yl]methyl]thio]-1H-benzimidazole hemihydrate

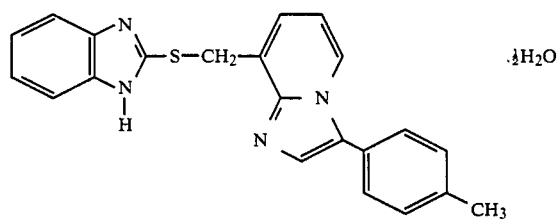

The title compound (1.58 g) was prepared by the method of Example 31 using 8.72 g (40 mmole) of 4-iodotoluene instead of 1-bromo-4-nitrobenzene and using triphenylphosphine instead of tri-o-tolylphosphine. Structure assignment was supported by the nmr and infrared spectra and by elemental analysis.

Analysis. Calcd. for $C_{22}H_{18}N_4S \cdot \frac{1}{2}H_2O$: C, 70.46; H, 4.97; N, 14.94; S, 8.55. Found: C, 70.64; H, 4.86; N, 15.19; S, 8.57.

Example 54

2-[[[3-(4-methylphenyl)imidazo[1,2-a]pyridin-8-yl]methyl]sulfinyl]-1H-benzimidazole

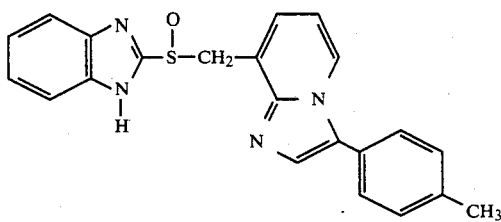

The title compound (801 mg) was prepared by the method of Example 2 using 1.38 g (3.7 mmole) of 2-[[[3-(4-methylphenyl)imidazo[1,2-a]pyridin-8-yl]methyl]thio]-1H-benzimidazole hemihydrate (see Example 53) instead of 2-[(imidazo[1,2-a]pyridin-8-yl)methyl)thio]-1H-benzimidazole. Structure assignment was supported by the nmr and infrared spectra and by elemental analysis.

Analysis. Calcd. for $C_{22}H_{18}N_4SO$: C, 68.37; H, 4.70; N, 14.50; S, 8.30. Found: C, 68.29; H, 4.60; N, 14.50; S, 8.33.

EXAMPLE 55

2-[(imidazo[1,2-a]pyridin-5-ylmethyl)thio]-1H-benzimidazole

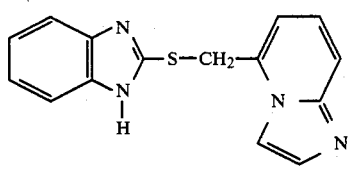

To a cold (ca. 0°) solution of 86.4 g (0.88 mole) of 2-amino-6-methylpyridine and 101 g (0.96 mole) of triethylamine in 1.0 liter of dichloromethane was added dropwise a solution of 106.1 g (0.88 mole) of trimethylacetyl chloride in 100 ml of dichloromethane. After stirring an hour after addition was completed, the mixture was poured into water and the layers separated. The aqueous layer was extracted with dichloromethane. The organic layers were combined and washed with water, dried over magnesium sulfate, filtered, and concentrated in vacuo to an oil that crystallized upon standing. The solid was triturated with hexane and collected by filtration, giving 115 g of 2-(trimethylacetamido)-6-methylpyridine. A 22.6 g (0.12 mmole) portion of the amide derivative was suspended in 250 ml of carbon tetrachloride containing 22.9 g (0.12 mmole) of N-bromosuccinimide and 100 mg of 2,2'-azobisisobutyronitrile. The mixture was heated at reflux under a sun lamp for one hour, after which insolubles were removed by filtration. The filtrate was concentrated in vacuo to an oil consisting of a mixture of the 6-bromomethyl-2-(trimethylacetamido)pyridine and 6-dibromomethyl-2-(trimethylacetamido)pyridine derivatives. The crude mixture was heated at reflux for fifteen minutes with 11.7 g (78 mmole) of 2-mercaptobenzimidazole in 300 ml of isopropyl alcohol. Upon cooling, a precipitate formed and was collected and washed with portions of isopropyl alcohol and diethyl ether. The trimethylacetyl group was removed by heating at reflux for four hours in 300 ml of 10% aqueous hydrochloric acid. After cooling, the mixture was concentrated in vacuo to an oil. The oil was dissolved in water and made alkaline with aqueous potassium carbonate. The oil that separated solidified upon addition of dichloromethane to the aqueous mixture. The solid was collected by filtration, washed with portions of water and dichloromethane, and air dried to yield 9.6 g of analytically pure 6-[(1H-benzimidazol-2-ylthio)methyl]-2-pyridinamine hemihydrate. (An additional 2.5 g of the title compound was isolated from the dichloromethane washes.) [Structure assignment was supported by the nmr and infrared spectra and by elemental analysis. Calcd. for $C_{13}H_{12}N_4S.\frac{1}{2}H_2O$: C, 58.84; H, 4.93; N, 21.11; S, 12.08. Found: C, 59.03; H, 4.40; N, 20.90; S, 12.30.] A mixture of 4.0 g (15.6 mmole) of 6-[(1H-benzimidazol-2-ylthio)methyl]-2-pyridinamine hemihydrate, 3.0 ml of 50% aqueous chloroacetaldehyde, and 2.5 g of sodium bicarbonate in ethanol was stirred at room temperature. After one day the mixture was filtered and the filtrate was concentrated in vacuo. Addition of dichloromethane induced crystallization. The solid was collected and air dried to yield 4.1 g of the title compound. Structure assignment was supported by the nmr and infrared spectra.

EXAMPLE 56

2-[(imidazo[1,2-a]pyridin-5-ylmethyl)sulfinyl]-1H-benzimidazole

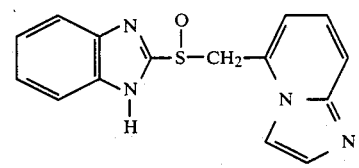

The title compound (1.7 g) was prepared by the method of Example 2 using 2.7 g (9.6 mmole) of 2-[(imidazo[1,2-a]pyridin-5-ylmethyl)thio]-1H-benzimidazole (see Example 55) instead of 2-[(imidazo[1,2-a]pyridin-8-ylmethyl)thio]1H-benzimidazole. Structure assignment was supported by the nmr and infrared spectra and by elemental analysis.

Analysis. Calcd. for $C_{15}H_{12}N_4SO$: C, 60.80; H, 4.08; N, 18.91; S, 10.82. Found: C, 60.64; H, 4.31; N, 18.53; S, 10.72.

EXAMPLE 57

| Table of Pharmacological Test Results. | | |
|---|---|---|
| Compound [Product of Example No.] | $(H^+K^+)-$ ATPase $IC_{50}$ (mcM) | Gastric-Fistula Beagle % Inhibition (3 mg/kg dose) |
| 3 | 2.7 | 57 i.d. |
| 5 | 6.7 | 16 i.d. |
| 7 | 8.5 | |
| 9 | 9.2 | |
| 11 | 6.2 | |
| 13 | 3.1 | |
| 15 | 4.8 | |
| 17 | 69.0 | |
| 19 | 5.0 | |
| 21 | 3.4 | |
| 23 | 6.2 | |
| 25 | 4.0 | |
| 28 | >100 | |
| 30 | 9.1 | |
| 33 | 17.5 | |

-continued

| Table of Pharmacological Test Results. | | |
| --- | --- | --- |
| Compound [Product of Example No.] | $(H^+K^+)-$ ATPase $IC_{50}$ (mcM) | Gastric-Fistula Beagle % Inhibition (3 mg/kg dose) |
| 36 | 6.9 | |
| 39 | 7.2 | |
| 42 | 15.2 | |
| 45 | 7.4 | |
| 47 | 13.0 | |
| 49 | 7.8 | |
| 52 | 5.5 | |
| 54 | 3.2 | |
| 56 | >100 | |

What is claimed is:

1. A compound of the formula:

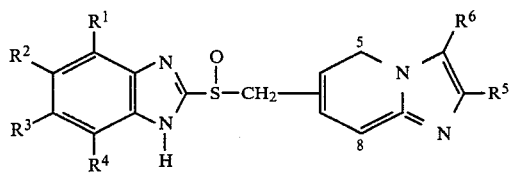

or the pharmaceutically acceptable acid addition salts thereof; or the pharmaceutically acceptable base addition salts thereof; wherein $R^1$, $R^2$, $R^3$, and $R^4$ are independently:

(a) hydrogen;
(b) $C_1$–$C_{10}$ alkyl;
(c) $C_1$–$C_6$ alkoxy;
(d) $C_1$–$C_4$ fluorinated alkyl; or
(e) halogen; and wherein $R^5$ and $R^6$ are independently:

(a) hydrogen;
(b) $C_1$–$C_{10}$ alkyl; or
(c) phenyl or phenyl substituted with 1 to 3 substituents selected from the group:
 (i) $C_1$–$C_{10}$ alkyl;
 (ii) $C_1$–$C_6$ alkoxy;
 (iii) $C_1$–$C_4$ fluorinated alkyl;
 (iv) halogen;
 (v) nitro, with the proviso that only one such substituent may be nitro; or
 (vi) $C_2$–$C_6$ alkoxycarbonyl.

2. A compound according to claim 1 having the formula:

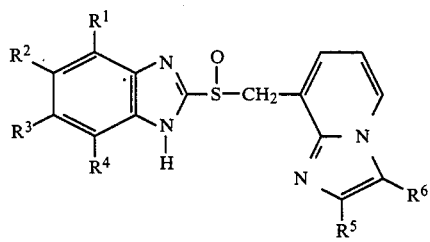

or the pharmaceutically acceptable acid addition salts thereof; or the pharmaceutically acceptable base addition salts thereof; wherein $R^1$, $R^2$, $R^3$, and $R^4$ are independently:

(a) hydrogen;
(b) $C_1$–$C_{10}$ alkyl;
(c) $C_1$–$C_6$ alkoxy;
(d) $C_1$–$C_4$ fluorinated alkyl; or
(e) halogen; and wherein $R^5$ and $R^6$ are independently:

(a) hydrogen;
(c) phenyl or phenyl substituted with 1 to 3 substituents selected from the group:
 (i) $C_1$–$C_{10}$ alkyl;
 (ii) $C_1$–$C_6$ alkoxy;
 (iii) $C_1$–$C_4$ fluorinated alkyl;
 (iv) halogen;
 (v) nitro, with the proviso that only one such substituent may be nitro; or
 (vi) $C_2$–$C_6$ alkoxycarbonyl.

3. A compound according to claim 2 having the formula:

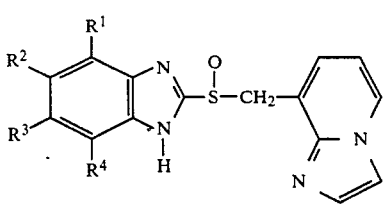

or the pharmaceutically acceptable acid addition salts thereof; or the pharmaceutically acceptable base addition salts thereof; wherein $R^1$, $R^2$, $R^3$, and $R^4$ are independently:

(a) hydrogen;
(b) $C_1$–$C_{10}$ alkyl;
(c) $C_1$–$C_6$ alkoxy;
(d) $C_1$–$C_4$ fluorinated alkyl; or
(e) halogen.

4. A compound according to claim 3 selected from the group consisting of:

2-[(imidazo[1,2-a]pyridin-8-ylmethyl)sulfinyl]-1H-benzimidazole,

2-[(imidazo[1,2-a]pyridin-8-ylmethyl)sulfinyl]-4-methyl-1H-benzimidazole,

2-[(imidazo[1,2-a]pyridin-8-ylmethyl)sulfinyl]-5-methyl-1H-benzimidazole,

2-[(imidazo[1,2-a]pyridin-8-ylmethyl)sulfinyl]-5,6-dimethyl-1H-benzimidazole,

2-[(imidazo[1,2-a]pyridin-8-ylmethyl)sulfinyl]-5-methoxy-1H-benzimidazole, 5-ethoxy-2-[(imidazo[1,2-a]pyridin-8-ylmethyl)sulfinyl]-1H-benzimidazole, 2-[(imidazo[1,2-a]pyridin-8-ylmethyl)sulfinyl]-5,6-dimethoxy-1H-benzimidazole, 5-chloro-2-[(imidazo[1,2-a]pyridin-8-ylmethyl)sulfinyl]-1H-benzimidazole, and 2-[(imidazo[1,2-a]pyridin-8-ylmethyl)sulfinyl]-5-(trifluoromethyl)-1H-benzimidazole; or the pharmaceutically acceptable acid addition salts thereof; or the pharmaceutically acceptable base addition salts thereof.

5. A compound according to claim 2 having the formula:

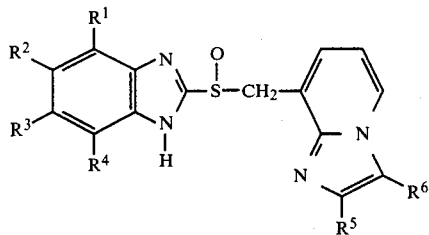

or the pharmaceutically acceptable acid addition salts thereof; or the pharmaceutically acceptable base addition salts thereof; wherein $R^1$, $R^2$, $R^3$, and $R^4$ are independently:
  (a) hydrogen;
  (b) $C_1$-$C_{10}$ alkyl;
  (c) $C_1$-$C_6$ alkoxy;
  (d) $C_1$-$C_4$ fluorinated alkyl; or
  (e) halogen; and
wherein $R^5$ and $R^6$ are independently:
  (a) hydrogen; or
  (b) $C_1$-$C_{10}$ alkyl, with the proviso that at least one of $R^5$ and $R^6$ is $C_1$-$C_{10}$ alkyl.

6. A compound according to claim 5 selected from the group consisting of:
2-[[(2-methylimidazo[1,2-a]pyridin-8-yl)methyl]sulfinyl]-1H-benzimidazole,
2-[[(3-methylimidazo[1,2-a]pyridin-8-yl)methyl]sulfinyl]-1H-benzimidazole, and
2-[[(2,3-dimethylimidazo[1,2-a]pyridin-8-yl)methyl]sulfinyl]-1H-benzimidazole; or the pharmaceutically acceptable acid addition salts thereof; or the pharmaceutically acceptable base addition salts thereof.

7. A compound according to claim 2 having the formula:

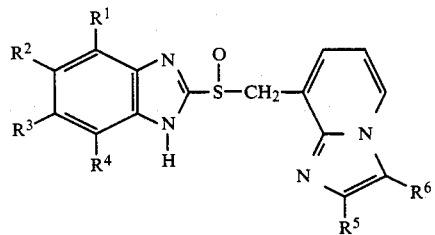

or the pharmaceutically acceptable acid addition salts thereof; or the pharmaceutically acceptable base addition salts thereof; wherein $R^1$, $R^2$, $R^3$, and $R^4$ are independently:
  (a) hydrogen;
  (b) $C_1$-$C_{10}$ alkyl;
  (c) $C_1$-$C_6$ alkoxy;
  (d) $C_1$-$C_4$ fluorinated alkyl; or
  (e) halogen; and
wherein one of $R^5$ and $R^6$ is hydrogen and the other of $R^5$ and $R^6$ is phenyl or phenyl substituted with 1 to 3 substituents selected from the group:
  (a) $C_1$-$C_{10}$ alkyl;
  (b) $C_1$-$C_6$ alkoxy;
  (c) $C_1$-$C_4$ fluorinated alkyl;
  (d) halogen;
  (e) nitro, with the proviso that only one such substituent may be nitro; or
  (f) $C_2$-$C_6$ alkoxycarbonyl.

8. A compound according to claim 7 having the formula:

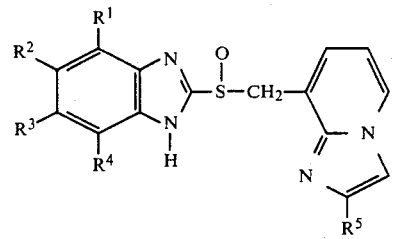

or the pharmaceutically acceptable acid addition salts thereof; or the pharmaceutically acceptable base addition salts thereof; wherein $R^1$, $R^2$, $R^3$, and $R^4$ are independently:
  (a) hydrogen;
  (b) $C_1$-$C_{10}$ alkyl;
  (c) $C_1$-$C_{16}$ alkoxy;
  (d) $C_1$-$C_4$ fluorinated alkyl; or
  (e) halogen; and
wherein $R^5$ is phenyl or phenyl substituted with 1 to 3 substituents selected from the group:
  (a) $C_1$-$C_{10}$ alkyl;
  (b) $C_1$-$C_6$ alkoxy;
  (c) $C_1$-$C_4$ fluorinated alkyl;
  (d) halogen;
  (e) nitro, with the proviso that only one such substituent may be nitro; or
  (f) $C_2$-$C_6$ alkoxycarbonyl.

9. A compound according to claim 8, which is 2-[[(2-phenylimidazo[1,2-a]pyridin-8-yl)methyl]sulfinyl]-1H-benzimidazole; or the pharmaceutically acceptable acid addition salts thereof; or the pharmaceutically acceptable base addition salts thereof.

10. A compound according to claim 7 having the formula:

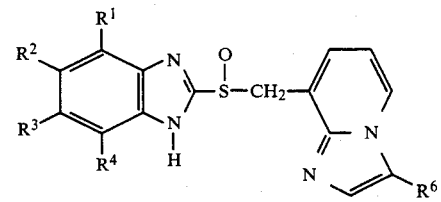

or the pharmaceutically acceptable acid addition salts thereof; or the pharmaceutically acceptable base addition salts thereof; wherein $R^1$, $R^2$, $R^3$, and $R^4$ are independently:
  (a) hydrogen;
  (b) $C_1$-$C_{10}$ alkyl;
  (c) $C_1$-$C_6$ alkoxy;
  (d) $C_1$-$C_4$ fluorinated alkyl; or
  (e) halogen; and
wherein $R^6$ is phenyl or phenyl substituted with 1 to 3 substituents selected from the group:
  (a) $C_1$-$C_{10}$ alkyl;
  (b) $C_1$-$C_6$ alkoxy;
  (c) $C_1$-$C_4$ fluorinated alkyl;
  (d) halogen;
  (e) nitro, with the proviso that only one such substituent may be nitro; or
  (f) $C_2$-$C_6$ alkoxycarbonyl.

11. A compound according to claim 10 selected from the group consisting of:
2-[[(3-phenylimidazo[1,2-a]pyridin-8-yl)methyl]sulfinyl]-1H-benzimidazole,
2-[[[3-(4-methylphenyl)imidazo[1,2-a]pyridin-8-yl]methyl]sulfinyl]-1H-benzimidazole,
2-[[[3-(4-chlorophenyl)imidazo[1,2-a]pyridin-8-yl]methyl]sulfinyl]-1H-benzimidazole,
2-[[[3-(4-nitrophenyl)imidazo[1,2-a]pyridin-8-yl]methyl]sulfinyl]-1H-benzimidazole,
2-[[[3-[3-(trifluoromethyl)phenyl]imidazo[1,2-a]pyridin-8-yl]methyl]sulfinyl]-1H-benzimidazole,
2-[[[3-[4-(trifluoromethyl)phenyl]imidazo[1,2-a]pyridin-8-yl]methyl]sulfinyl]-1H-benzimidazole,
methyl 4-[8-[(1H-benzimidazol-2-ylsulfinyl)methyl]imidazo[1,2-a]pyridin-3-yl]benzoate,
5-methyl-2-[[[3-[3-(trifluoromethyl)phenyl]imidazo[1,2-a]pyridin-8-yl]methylsulfinyl)-1H-benzimidazole,
5-chloro-2-[[[3-[3-(trifluoromethyl)phenyl]imidazo[1,2-a]pyridin-8-yl]methyl]sulfinyl]-1H-benzimidazole, and
5-chloro-2-[[[3-[4-(trifluoromethyl)phenyl]imidazo[1,2-a]pyridin-8-yl]methyl]sulfinyl]-1H-benzimidazole;
or the pharmaceutically acceptable acid addition salts thereof; or the pharmaceutically acceptable base addition salts thereof.

12. A compound according to claim 1 having the formula:

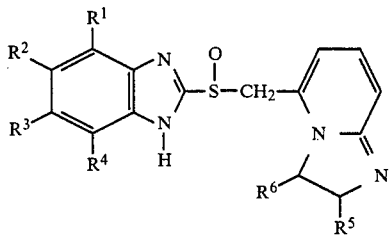

or the pharmaceutically acceptable acid addition salts thereof; or the pharmaceutically acceptable base addition salts thereof; wherein $R^1$, $R^2$, $R^3$, and $R^4$ are independently:
  (a) hydrogen;
  (b) $C_1$–$C_{10}$ alkyl;
  (c) $C_1$–$C_6$ alkoxy;
  (d) $C_1$–$C_4$ fluorinated alkyl; or
  (e) halogen; and
wherein $R^5$ and $R^6$ are independently:
  (a) hydrogen;
  (b) $C_1$–$C_{10}$ alkyl; or
  (c) phenyl or phenyl substituted with 1 to 3 substituents selected from the group:
    (i) $C_1$–$C_{10}$ alkyl;
    (ii) $C_1$–$C_6$ alkoxy;
    (iii) $C_1$–$C_4$ fluorinated alkyl;
    (iv) halogen;
    (v) nitro, with the proviso that only one such substituent may be nitro; or
    (vi) $C_2$–$C_6$ alkoxycarbonyl.

13. A compound according to claim 12, which is 2-[(imidazo[1,2-a]pyridin-5-ylmethyl]sulfinyl]-1H-benzimidazole; or the pharmaceutically acceptable acid addition salts thereof; or the pharmaceutically acceptable base addition salts thereof.

14. A pharmaceutical composition useful in the treatment of ulcers in mammals comprising a pharmaceutically effective amount of at least one compound according to claim 1, together with one or more non-toxic pharmaceutically acceptable carriers.

15. A pharmaceutical composition according to claim 14 wherein said compound is selected from the group consisting of:
2-[(imidazo[1,2-a]pyridin-8-ylmethyl)sulfinyl]-1H-benzimidazole,
2-[(imidazo[1,2-a]pyridin-8-ylmethyl)sulfinyl]-4-methyl-1H-benzimidazole,
2-[(imidazo[1,2-a]pyridin-8-ylmethyl)sulfinyl]-5-methyl-1H-benzimidazole,
2-[(imidazo[1,2-a]pyridin-8-ylmethyl)sulfinyl]-5,6-dimethyl-1H-benzimidazole,
2-[(imidazo[1,2-a]pyridin-8-ylmethyl)sulfinyl]-5-methoxy-1H-benzimidazole,
5-methoxy-2-[(imidazo[1,2-a]pyridin-8-ylmethyl)sulfinyl]-1H-benzimidazole,
2-[(imidazo[1,2-a]pyridin-8-ylmethyl)sulfinyl]-5,6-dimethoxy-1H-benzimidazole,
5-chloro-2-[(imidazo[1,2-a]pyridin-8-ylmethyl)sulfinyl]-1H-benzimidazole,
2-[(imidazo[1,2-a]pyridin-8-ylmethyl)sulfinyl]-5-(trifluoromethyl)-1H-benzimidazole,
2-[[(2-methylimidazo[1,2-a]pyridin-8-yl)methyl]sulfinyl]-1H-benzimidazole,
2-[[(3-methylimidazo[1,2-a]pyridin-8-yl)methyl]sulfinyl]-1H-benzimidazole,
2-[[(2,3-dimethylimidazo[1,2-a]pyridin-8-yl)methyl]sulfinyl]-1H-benzimidazole,
2-[[(2-phenylimidazo[1,2-a]pyridin-8-yl)methyl]sulfinyl]-1H-benzimidazole,
2-[[(3-phenylimidazo[1,2-a]pyridin-8-yl)methyl]sulfinyl]-1H-benzimidazole,
2-[[[3-(4-methylphenyl)imidazo[1,2-a]pyridin-8-yl]methyl]-sulfinyl]-1H-benzimidazole,
2-[[[3-(4-chlorophenyl)imidazo[1,2-a]pyridin-8-yl]methyl]sulfinyl]-1H-benzimidazole,
2-[[[3-(4-nitrophenyl)imidazo[1,2-a]pyridin-8-yl]methyl]sulfinyl]-1H-benzimidazole,
2-[[[3-(3-(trifluoromethyl)phenyl]imidazo[1,2-a]pyridin-8-yl]methyl]sulfinyl]-1H-benzimidazole,
2-[[[3-[4-(trifluoromethyl)phenyl]imidazo[1,2-a]pyridin-8-yl]methyl]sulfinyl]-1H-benzimidazole,
methyl 4-[8-[(1H-benzimidazol-2-ylsulfinyl)methyl]imidazo[1,2-a]pyridin-3-yl)benzoate,
5-methyl-2-[[[3-[3-(trifluoromethyl)phenyl]imidazo[1,2-a]pyridin-8-yl]methyl]sulfinyl]-1H-benzimidazole,
5-chloro-2-[[[3-[3-(trifluoromethyl)phenyl]imidazo[1,2-a]pyridin-8-yl]methyl]sulfinyl]-1H-benzimidazole,
5-chloro-2-[[[3-[4-(trifluoromethyl)phenyl]imidazo[1,2a]pyridin-8-yl]methyl]sulfinyl]-1H-benzimidazole, and 2-[(imidazo[1,2-a]pyridin-5-ylmethyl)sulfinyl]-1H-benzimidazole; or the pharmaceutically acceptable acid addition salts thereof; or the pharmaceutically acceptable base addition salts thereof.

16. A method for treating ulcers in mammals comprising administering a therapeutically effective amount of at least one compound of claim 1 to a mammal in need of such treatment.

17. A method according to claim 16 wherein said compound is selected from the group consisting of:
2-[(imidazo[1,2-a]pyridin-8-ylmethyl)sulfinyl]-1H-benzimidazole,
2-[(imidazo[1,2-a]pyridin-8-ylmethyl)sulfinyl]-4-methyl-1H-benzimidazole, 2-[(imidazo[1,2-a]pyridin-8-ylmethyl)sulfinyl]-5-methyl-1H-benzimidazole,
2-[(imidazo[1,2a]pyridin-8-ylmethyl)sulfinyl]-5,6-dimethyl-1H-benzimidazole,
2-[(imidazo[1,2-a]pyridin-8-ylmethyl)sulfinyl]-5-methoxy-1H-benzimidazole,
5-methoxy-2-[(imidazo[1,2-a)pyridin-8-ylmethyl)sulfinyl]-1H-benzimidazole,
2-[(imidazo[1,2-a]pyridin-8-ylmethyl)sulfinyl]-5,6-dimethoxy-1H-benzimidazole,
5-chloro-2-[(imidazo[1,2-a]pyridin-8-ylmethyl)sulfinyl]-1H-benzimidazole,
2-[(imidazo[1,2-a]pyridin-8-ylmethyl)sulfinyl]-5-(trifluoromethyl)-1H-benzimidazole,
2-[[(2-methylimidazo[1,2-a]pyridin-8-yl)methyl]sulfinyl]1H-benzimidazole,
2-[[(3-methylimidazo[1,2-a]pyridin-8-yl)methyl]sulfinyl)1H-benzimidazole,
2-[[(2,3-dimethylimidazo[1,2-a]pyridin-8-yl)methyl]-sulfinyl]-1H-benzimidazole,
2-[[(2-phenylimidazo[1,2-a]pyridin-8-yl)methyl]sulfinyl]1H-benzimidazole,
2-[[(3-phenylimidazo[1,2-a]pyridin-8-yl)methyl]sulfinyl]-1H-benzimidazole,
2-[[[3-(4-methylphenyl)imidazo[1,2-a]pyridin-8-yl]methyl]sulfinyl]-1H-benzimidazole,
2-[[[3-(4-chlorophenyl)imidazo[1,2-a]pyridin-8-yl]methyl]sulfinyl]-1H-benzimidazole,
2-[[[3-(4-nitrophenyl)imidazo[1,2-a]pyridin-8-yl]methyl]sulfinyl]-1H-benzimidazole,
2-[[[3-[3-(trifluoromethyl)phenyl]imidazo[1,2-a]pyridin-8-yl]methyl]sulfinyl]-1H-benzimidazole,
2-[[[3-[4-(trifluoromethyl)phenyl]imidazo[1,2-a]pyridin-8-yl]methyl]sulfinyl]-1H-benzimidazole,
methyl 4-[8-[(1H-benzimidazol-2-ylsulfinyl)methyl]imidazo[1,2-a]pyridin-3-yl]benzoate,
5-methyl-2-[[[3-[3-(trifluoromethyl)phenyl]imidazo[1,2-a]pyridin-8-yl]methyl]sulfinyl]-1H-benzimidazole,
5-chloro-2-[[[3-[3-(trifluoromethyl)phenyl]imidazo[1,2-a]pyridin-8-yl]methyl]sulfinyl]-1H-benzimidazole,
5-chloro-2-[[[3-[4-(trifluoromethyl)phenyl]imidazo[1,2-a]pyridin-8-yl]methyl]sulfinyl]-1H-benzimidazole and
2-[(imidazo[1,2-a]pyridin-5-ylmethyl)sulfinyl]-1H-benzimidazole; or the pharmaceutically acceptable acid addition salts thereof; or the pharmaceutically acceptable base addition salts thereof.

18. A method for treating ulcers in mammals comprising administering a therapeutically effective amount of a pharmaceutical composition of claim 15 to a mammal in need of such treatment.

* * * * *

UNITED STATES PATENT AND TRADEMARK OFFICE
CERTIFICATE OF CORRECTION

PATENT NO. : 4,687,775
DATED : August 18, 1987
INVENTOR(S) : Adelstein, et. al.

Page 1 of 4

It is certified that error appears in the above-identified patent and that said Letters Patent is hereby corrected as shown below:

Column 4, Scheme A, the last two structures (lines 30-47), reading

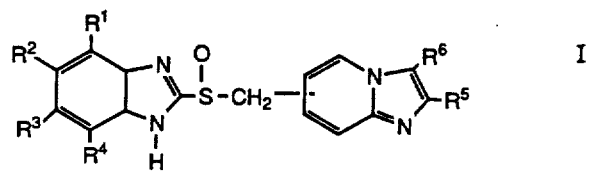     I

+

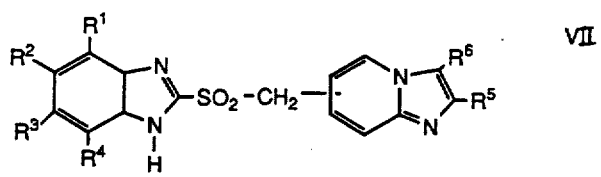     VII should read

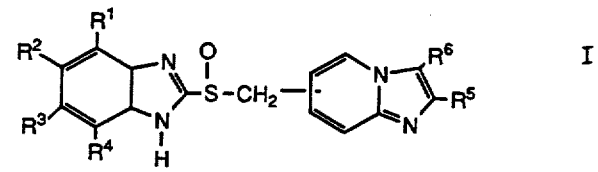     I

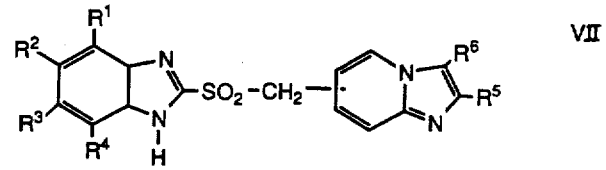     VII

UNITED STATES PATENT AND TRADEMARK OFFICE
CERTIFICATE OF CORRECTION

PATENT NO. : 4,687,775

DATED : August 18, 1987

INVENTOR(S) : Adelstein, et. al.

It is certified that error appears in the above-identified patent and that said Letters Patent is hereby corrected as shown below:

Column 7, Scheme B, lines 34-41, reading

Column 7, line 66, reading "Preferred alcoholic mixture" should read -- Preferred cyclization conditions include heating an aqueous or alcoholic mixture --.

Column 11, line 36, reading "$(H^+K^+)-$" should read -- $(H^+ +K^+)-$ --.

Column 31, lines 44-45, reading "$(CH_3CHhd2)_2O:$" should read -- $(CH_3CH_2)_2O:$ --.

Column 32, line 55, reading "(400 mmole)" should read -- (40 mmole) --.

Column 38, Example 57, line 53, reading "$(H^+K^+)-$" should read -- $(H^+ +K^+)-$ --.

UNITED STATES PATENT AND TRADEMARK OFFICE
CERTIFICATE OF CORRECTION

PATENT NO. : 4,687,775

DATED : August 18, 1987

INVENTOR(S) : Adelstein, et. al.

It is certified that error appears in the above-identified patent and that said Letters Patent is hereby corrected as shown below:

Column 39, line 4, reading "$(H^+K^+)-$" should read -- $(H^+ + K^+)-$ --.

Column 40, lines 5-6, reading

"(a) hydrogen;

(c) phenyl or phenyl substituted..."

should read (a) hydrogen;

(b) $C_1-C_{10}$ alkyl; or (c) phenyl or phenyl substituted..."

Column 44, line 16, reading "5-methoxy-2" should read -- 5-ethoxy-2 --.

UNITED STATES PATENT AND TRADEMARK OFFICE
CERTIFICATE OF CORRECTION

PATENT NO. : 4,687,775
DATED : August 18, 1987
INVENTOR(S) : Adelstein, et al

It is certified that error appears in the above-identified patent and that said Letters Patent is hereby corrected as shown below:

Column 45, line 7, reading "5-methoxy-2" should read -- 5-ethoxy-2 --.

Signed and Sealed this

Twenty-first Day of November, 1989

*Attest:*

JEFFREY M. SAMUELS

*Attesting Officer*   *Acting Commissioner of Patents and Trademarks*